United States Patent
Koob et al.

(10) Patent No.: US 9,943,551 B2
(45) Date of Patent: Apr. 17, 2018

(54) TISSUE GRAFTS COMPOSED OF MICRONIZED PLACENTAL TISSUE AND METHODS OF MAKING AND USING THE SAME

(71) Applicant: MiMedx Group, Inc., Marietta, GA (US)

(72) Inventors: Thomas J. Koob, Marietta, GA (US); John Daniel, Marietta, GA (US); Randall Spencer, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 0 days.

(21) Appl. No.: 13/815,784

(22) Filed: Mar. 15, 2013

(65) Prior Publication Data

US 2014/0052274 A1 Feb. 20, 2014

Related U.S. Application Data

(60) Provisional application No. 61/683,698, filed on Aug. 15, 2012.

(51) Int. Cl.
*A61K 35/50* (2015.01)

(52) U.S. Cl.
CPC .................... *A61K 35/50* (2013.01)

(58) Field of Classification Search
CPC .......... A61F 2/02; A61F 2/0063; A61L 27/36; A61L 27/3604; A61L 27/3633; A61L 27/3641; A61L 27/3683; A61L 27/38; A61L 27/3804; A61L 27/3839; A61L 27/3843; A61K 35/50

USPC ......... 623/23.71, 23.72, 23.73, 23.74, 23.75, 623/23.76

See application file for complete search history.

(56) References Cited

U.S. PATENT DOCUMENTS

| | | | |
|---|---|---|---|
| 2,694,914 A | 11/1954 | Glover, Jr. | |
| 3,272,204 A | 9/1966 | Artandi | |
| 4,564,368 A | 1/1986 | Sawyer et al. | |
| 4,745,771 A | 5/1988 | Linner et al. | |
| 4,968,325 A | 11/1990 | Black et al. | |
| 5,118,867 A | 6/1992 | Bahrmann et al. | |
| 5,284,655 A | 2/1994 | Bogdansky et al. | |
| 5,541,232 A | 7/1996 | Howell et al. | |
| 5,807,581 A | 9/1998 | Rosenblatt et al. | |
| 6,030,635 A | 2/2000 | Gertzman et al. | |
| 6,387,369 B1 | 5/2002 | Pittenger et al. | |
| 6,565,960 B2 | 5/2003 | Koob et al. | |

(Continued)

FOREIGN PATENT DOCUMENTS

| | | |
|---|---|---|
| CN | 101433556 | 5/2009 |
| EP | 0 431 164 | 6/1991 |

(Continued)

OTHER PUBLICATIONS

U.S. Appl. No. 13/647,308, filed Oct. 8, 2012, Daniel et al.

(Continued)

*Primary Examiner* — David Isabella
*Assistant Examiner* — Rokhaya Diop
(74) *Attorney, Agent, or Firm* — Alston & Bird LLP

(57) ABSTRACT

Described herein are tissue grafts composed of at least one membrane, where at least one side of the membrane has micronized placental tissue applied it. Also described herein are methods for making and using the tissue grafts.

15 Claims, 12 Drawing Sheets

(56) References Cited

U.S. PATENT DOCUMENTS

| | | |
|---|---|---|
| 6,716,895 B1 | 4/2004 | Terry |
| 6,936,271 B1 | 8/2005 | Oliver et al. |
| 7,101,857 B2 | 9/2006 | Sung et al. |
| 7,311,904 B2 | 12/2007 | Hariri |
| 7,311,905 B2 | 12/2007 | Hariri |
| 7,871,646 B2 | 1/2011 | Ghinelli |
| 7,901,455 B2 | 3/2011 | Koob et al. |
| 8,067,044 B2 | 11/2011 | Henry et al. |
| 8,153,162 B2 | 4/2012 | Tseng et al. |
| 8,177,839 B2 | 5/2012 | Koob et al. |
| 8,192,481 B2 | 6/2012 | King |
| 8,323,701 B2 | 12/2012 | Daniel et al. |
| 8,357,403 B2 | 1/2013 | Daniel et al. |
| 8,372,439 B2 | 2/2013 | Daniel et al. |
| 8,623,421 B2 | 1/2014 | Daniel |
| 2002/0123141 A1 | 9/2002 | Hariri |
| 2002/0160510 A1 | 10/2002 | Hariri |
| 2003/0032179 A1 | 2/2003 | Hariri |
| 2003/0187515 A1 | 10/2003 | Hariri et al. |
| 2004/0026244 A1 | 2/2004 | Hodges et al. |
| 2004/0048796 A1* | 3/2004 | Hariri et al. ............... 514/12 |
| 2006/0140913 A1 | 6/2006 | Bhatia |
| 2006/0166361 A1 | 7/2006 | Seyda et al. |
| 2006/0210532 A1 | 9/2006 | Carmeliet et al. |
| 2007/0020225 A1 | 1/2007 | Abramson et al. |
| 2007/0021762 A1 | 1/2007 | Liu et al. |
| 2007/0071740 A1 | 3/2007 | Tseng et al. |
| 2007/0071828 A1 | 3/2007 | Tseng et al. |
| 2007/0202189 A1 | 8/2007 | Ahlfors |
| 2007/0248575 A1 | 10/2007 | Connor et al. |
| 2007/0299043 A1 | 12/2007 | Hunter et al. |
| 2008/0046095 A1 | 2/2008 | Daniel |
| 2008/0050347 A1 | 2/2008 | Ichim |
| 2008/0069895 A1 | 3/2008 | Liu et al. |
| 2008/0131966 A1 | 6/2008 | Hariri |
| 2008/0181935 A1 | 7/2008 | Bhatia et al. |
| 2008/0181967 A1* | 7/2008 | Liu et al. ............... 424/583 |
| 2008/0233552 A1 | 9/2008 | Ma et al. |
| 2009/0012629 A1 | 1/2009 | Yao et al. |
| 2009/0036996 A1 | 2/2009 | Roeber |
| 2009/0053290 A1 | 2/2009 | Sand et al. |
| 2009/0092664 A1 | 4/2009 | Mumper et al. |
| 2009/0142831 A1 | 6/2009 | Hariri |
| 2009/0287308 A1 | 11/2009 | Davis et al. |
| 2009/0291891 A1 | 11/2009 | Neufeld |
| 2010/0028849 A1 | 2/2010 | Shelby et al. |
| 2010/0104539 A1* | 4/2010 | Daniel ............... A61L 27/3604 424/93.7 |
| 2010/0136114 A1 | 6/2010 | Mao |
| 2010/0143312 A1 | 6/2010 | Hariri et al. |
| 2010/0178297 A1 | 7/2010 | Carmeliet et al. |
| 2010/0209408 A1 | 8/2010 | Stephen et al. |
| 2010/0260847 A1 | 10/2010 | Hariri |
| 2010/0272782 A1 | 10/2010 | Owens et al. |
| 2010/0317677 A1 | 12/2010 | Hassel et al. |
| 2011/0044997 A1 | 2/2011 | Rankin et al. |
| 2011/0177150 A1 | 7/2011 | Pathak et al. |
| 2011/0189301 A1 | 8/2011 | Yang et al. |
| 2011/0206776 A1* | 8/2011 | Tom et al. ............... 424/583 |
| 2011/0282448 A1 | 11/2011 | Paulos et al. |
| 2011/0307059 A1 | 12/2011 | Young et al. |
| 2012/0010708 A1 | 1/2012 | Young et al. |
| 2012/0030963 A1 | 2/2012 | Durance et al. |
| 2012/0078378 A1 | 3/2012 | Daniel et al. |
| 2012/0135045 A1 | 5/2012 | Nixon et al. |
| 2012/0189571 A1 | 7/2012 | Sengupta et al. |
| 2012/0189583 A1 | 7/2012 | Liu et al. |
| 2012/0189586 A1 | 7/2012 | Harrell |
| 2012/0282348 A1 | 11/2012 | Yates et al. |
| 2012/0294910 A1 | 11/2012 | Daniel et al. |
| 2013/0230561 A1 | 9/2013 | Daniel et al. |
| 2013/0273008 A1 | 10/2013 | Lemper et al. |
| 2014/0142041 A1 | 5/2014 | Koob |
| 2014/0205646 A1 | 7/2014 | Morse et al. |
| 2014/0255496 A1 | 9/2014 | Daniel et al. |
| 2014/0255508 A1 | 9/2014 | Morse et al. |
| 2014/0302162 A1 | 10/2014 | Morse et al. |
| 2014/0308233 A1 | 10/2014 | Koob |
| 2014/0356451 A1 | 12/2014 | Koob |
| 2015/0127116 A1 | 5/2015 | Pringle et al. |
| 2016/0030633 A1 | 2/2016 | Daniel et al. |

FOREIGN PATENT DOCUMENTS

| | | | |
|---|---|---|---|
| EP | 0431479 A1 | 6/1991 | |
| EP | 0 506 207 B1 | 9/1992 | |
| JP | 2007-106760 | 4/2007 | |
| KR | 10/1991/0011272 | 8/1991 | |
| KR | 10/1991/0011727 | 8/1991 | |
| KR | 2001/100588 | 11/2001 | |
| WO | WO-88/03805 A1 | 6/1988 | |
| WO | WO-01/00151 A1 | 1/2001 | |
| WO | WO-01/08716 A1 | 2/2001 | |
| WO | WO-2004/026244 | 4/2004 | |
| WO | WO 2004026244 A2 * | 4/2004 | ............ A61K 35/50 |
| WO | WO-2005/017165 | 2/2005 | |
| WO | WO-2007/010305 | 1/2007 | |
| WO | WO-2007/083984 A1 | 7/2007 | |
| WO | WO-2009/033160 A1 | 3/2009 | |
| WO | WO-2009/048908 | 4/2009 | |
| WO | WO-2009/132186 A1 | 10/2009 | |
| WO | WO-2010/029344 A2 | 3/2010 | |
| WO | WO-2011/103470 | 8/2011 | |
| WO | WO-2011/127117 | 10/2011 | |
| WO | WO-2012/003377 | 1/2012 | |
| WO | WO-2012/065937 A1 | 5/2012 | |
| WO | WO-2012/069559 A1 | 5/2012 | |
| WO | WO-2012/112410 A2 | 8/2012 | |
| WO | WO-2012/112417 A2 | 8/2012 | |
| WO | WO-2012/112441 A1 | 8/2012 | |
| WO | WO-2012/170905 | 12/2012 | |
| WO | WO-2013/095830 A1 | 6/2013 | |

OTHER PUBLICATIONS

U.S. Appl. No. 13/688,091, filed Nov. 28, 2012, Spencer et al.
U.S. Appl. No. 13/719,148, filed Feb. 13, 2012, Morse et al.
U.S. Appl. No. 13/744,331, filed Jan. 17, 2013, Koob et al.
U.S. Appl. No. 13/744,332, filed Jan. 17, 2013, Pringle et al.
U.S. Appl. No. 13/745,642, filed Jan. 18, 2013, Koob et al.
U.S. Appl. No. 13/787,612, filed Mar. 6, 2013, Morse et al.
U.S. Appl. No. 13/815,747, filed Mar. 15, 2013, Daniel et al.
U.S. Appl. No. 13/815,753, filed Mar. 15, 2013, Koob et al.
U.S. Appl. No. 13/815,873, filed Mar. 15, 2013, Brown et al.
U.S. Appl. No. 13/963,984, filed Aug. 9, 2013, Daniel et al.
U.S. Appl. No. 13/967,326, filed Aug. 14, 2013, Koob et al.
U.S. Appl. No. 13/983,301, filed Feb. 13, 2012, Morse et al.
U.S. Appl. No. 14/050,218, filed Oct. 9, 2013, Brown et al.
"MiMedx Group Announces Launch of EpiFixTM and Hiring of Vice President, Wound Care," Mimedx Press Release (2011).
Autiero et al., "Placental growth factor and its receptor, vascular endothelial growth factor receptor-1:novel targets for stimulation of ischemic tissue revascularization and inhibition of angiogenic and inflammatory disorders," J. Thromb. Haemo., (2003), 1:1356-1370.
EpiFix Product Brochure (2011).
Hannallah et al., "Cerebrospinal fluid leaks following cervical spine surgery," J. Bone Joint Surg. Am., (2008), 90(5):1101-1105.
Hattori et al., "Placental growth factor reconstitutes hematopoiesis by recruiting VEGFR1+ stem cells from bone-marrow microenvironment," Nat. Med., (2002), 8(8):841-849.
Khan et al., "Postoperative management protocol for incidental dural tears during degenerative lumbar spine surgery: A review of 3,183 consecutive degenerative lumbar cases," Spine (Phila Pa 1976), (2006), 31(22):2609-2613.
Mayfield et al., "Watertight closure of spinal dura mater: Technical note," J. Neurosurg., (1975), 43(5):639-640.
PCT International Preliminary Report on Patentability for copending PCT Application No. PCT/US2012/024798, dated Feb. 1, 2013.
PCT International Search Report and Written Opinion for copending PCT Application No. PCT/US2013/054319, dated Nov. 13, 2013.

(56) References Cited

OTHER PUBLICATIONS

PCT International Search Report and Written Opinion for copending PCT Application No. PCT/US2013/055003, dated Nov. 19, 2013.
PCT International Search Report and Written Opinion for copending PCT Application No. PCT/US2013/054320, dated Nov. 6, 2013.
PCT International Search Report and Written Opinion for copending PCT Application No. PCT/US2013/054322, dated Oct. 22, 2013.
PCT International Search Report and Written Opinion for copending PCT Application No. PCT/US2012/66862, dated Feb. 12, 2013.
PCT International Search Report and Written Opinion for copending PCT Application No. PCT/US2013/054325, dated Oct. 28, 2013.
PCT International Search Report for copending PCT Application No. PCT/US2012/024798, dated Jun. 20, 2012.
Tao, et al., "Implantation of amniotic membrane to reduce postlaminectomy epidurla adhesions," Eur. Spine. J., (2009), 18:1202-1212.
Koob et al., "Biological properties of dehydrated human amnion-chorion composite graft: implications for chronic wound healing", International Wound Healing, 2013, 10(5):493-500.
PCT International Search Report and Written Opinion dated Jan. 9, 2014 in related PCT Patent Application No. PCT/US2013/064146.
MiMedx Press Release, "MiMedx Scientific Study is Electronically Published in the International Wound Journal", 2013.
http://proxybiomedical.com/Images/ML005-01-Rev002.pdf (accessed on Jun. 5, 2014.).
International Search Report and Written Opinion for PCT/US2014/012141, dated May 20, 2014.
Nagaya et al., "Transplantation of mesenchymal stem cells improves cardiac function in a rat model of dilated cardiomyopathy", Circulation, 2005, 112(8):1128-1135.
Parolini et al., "Toward cell therapy using placenta-derived cells: disease mechanisms, cell biology, preclinical studies, and regulatory aspects at the round table", Stem Cells and Development, 2010, 19(2):143-154.
PCT International Preliminary Report on Patentability dated Jan. 16, 2014 in related PCT Patent Application No. PCT/US12/66862.
PCT International Search Report and Written Opinion, PCT Appl. PCT/US2013/063736, dated Aug. 12, 2014.
U.S. Appl. No. 61/543,995, filed Oct. 6, 2011, Daniel et al.
Database WPI XP002732611 & KR 2001-0100588, dated Nov. 14, 2001—Abstract.
Extended European Search Report dated Dec. 2, 2014, for European Patent Application No. EP 12746721.
Lu. et al., "Molecular mechanisms and clinical applications of nordihydroguaiaretic acid (NDGA) and its derivatives: An update," Med. Sci. Monit., (2010), 16(5):RA93-RA100.
Moussy et al., "Transport characteristics of a novel local drug delivery system using nordihydroguaiaretic acid (NDGA)-polymerized collagen fibers," Biotechnology Progress, (2007), 23(4):990-994.
PCT International Preliminary Report on Patentability dated Nov. 28, 2014, for International Patent Application No. PCT/US2013/054319.
International Preliminary Report of Patentability dated Feb. 17, 2015 for PCT Application No. PCT/US2013/054320.
PCT International Preliminary Report on Patentability dated Nov. 27, 2014, for International Patent Application No. PCT/US2013/055003.
PCT International Preliminary Report on Patentability dated Dec. 8, 2014, for International Patent Application No. PCT/US2013/054322.
PCT International Preliminary Report on Patentability dated Feb. 14, 2013 in PCT Patent Application No. PCT/US2012/024814.
PCT International Search Report and Written Opinion for PCT Patent Application No. PCT/US2012/024814 dated Aug. 16, 2012.
PCT International Preliminary Report on Patentability dated Dec. 30, 2014, for International Patent Application No. PCT/US2013/063736.
PCT International Search Report and Written Opinion for PCT Application No. PCT/US2012/065672, dated Feb. 8, 2013.
PCT International Preliminary Report of Patentability for PCT Patent Application PCT/US2013/064146, dated Sep. 25, 2014.
PCT International Search Report and Written Opinion for PCT Application No. PCT/US2015/12087, dated Apr. 13, 2015.
PCT International Search Report and Written Opinion for PCT/US2014/012141, dated May 20, 2014.
PCT International Preliminary Report on Patentability dated Nov. 10, 2014 in PCT Patent Application No. PCT/US2013/067623.
PCT International Search Report and Written Opinion dated Apr. 21, 2014 in PCT Patent Application No. PCT/US13/67623.
PCT International Preliminary Report on Patentability dated Dec. 30, 2014 in PCT Patent Application No. PCT/US13/67622.
PCT International Search Report and Written Opinion dated Apr. 16, 2014 in PCT Patent Application No. PCT/US13/67622.
PCT International Search Report and Written Opinion dated Apr. 22, 2014 in PCT Patent Application No. PCT/US13/67620.
PCT International Search Report and Written Opinion dated Aug. 26, 2014 in PCT Patent Application No. PCT/US2014/033346.
PCT International Preliminary Report of Patentability for PCT Application No. PCT/US14/28975 dated Feb. 6, 2015.
PCT International Search Report and Written Opinion dated Jul. 24, 2014 in PCT Patent Application No. PCT/US2014/028975.
PCT International Search Report and Written Opinion dated Dec. 30, 2014 in PCT Patent Application No. PTC/US2014/054603.
PCT International Search Report and Written Opinion dated Dec. 29, 2014 for PCT Patent Application PCT/US2014/053270.
PCT International Preliminary Report on Patentability dated Dec. 3, 2014 in PCT Patent Application No. PCT/US2013/067618.
PCT International Search Report and Written Opinion dated Apr. 22, 2014 in PCT Patent Application No. PCT/US13/67618.
U.S. Appl. No. 14/719,581, filed May 22, 2015, Daniel, el al.
AzoMaterials. Particle Size—US Sieve Series and Tyler Mesh Size Equivalents. Datasheet [online]. AZoM.com, Copyright 2000-2015. Updated Jun. 11, 2013 [retrieved on Sep. 24, 2015]. Retrieved from the Internert: URL:http://www.azom.com/article.aspx?ArticleID=1417.
Kim et al., "Wharton's Jelly-Derived Mesenchymal Stem Cells: Phenotypic Characterization and Optimizing Their Therapeutic Potential for Clinical Applications", 2013, Int. J. Mol. Sci., 14, pp. 11692-11712, specifically p. 11694.
Mardovin et al., "The "Super" Expansion Graft", J Burn Care Rehabil, Sep./Oct. 1992, pp. 556-559 vol. 13, No. 5, pp. 556-559.
MiMedx: "PURION Processed Dehydrated Human Amnion/Chorion Membrane Allografts Introduction," Jul. 2012.
Rasenack, N. et al., "Micron-size drug particles: common and novel micronization techniques", Pharmaceutical Development and Technology, 2004, 9(1): 1-13.
Stedman's Online Dictionary. Bursa. Datasheet [online]. Lippincott Williams & Wilkins Copyright 2009 [retrieved on Sep. 24, 2015]. Retrieved from the internet: <URL:http://www.azom.com/article.aspx?ArticleD=1417>p. 2.
Uchide et al., "Possible Roles of Proinflammatory and Chemoattractive Cytokines Produced by Human Fetal Membrane Cells in the Pathology of Adverse Pregnancy Outcomes Associated with Influenza Virus Infection", Mediators of Inflammation, 2012, vol. 2012; Article ID 270670, 32 pages.

\* cited by examiner

TISSUE GRAFTS COMPOSED OF MICRONIZED PLACENTAL TISSUE AND METHODS OF MAKING AND USING THE SAME

CROSS-REFERENCE TO RELATED APPLICATIONS

This application claims priority to U.S. provisional patent application No. 61/683,698, filed on Aug. 15, 2012. The content of the prior application is incorporated herein by reference in its entirety.

BACKGROUND OF THE INVENTION

Placental tissue is known in the art as a basis for wound coverings. Typically, the placental tissue is harvested after an elective Cesarean surgery. The placenta or amniotic sac, which is commonly referred to as the amniotic membrane, has two primary layers of tissue, amnion and chorion. Amnion tissue is the innermost layer of the amniotic sac and in direct contact with the amniotic fluid. The amniotic sac contains the amniotic fluid and protects the fetal environment. Histological evaluation indicates that the membrane layers of the amnion consist of single layer of epithelium cells, thin reticular fibers (basement membrane), a thick compact layer, and fibroblast layer. The fibrous layer of amnion (i.e., the basement membrane) contains collagen types IV, V, and VII, and cell-adhesion bio-active factors including fibronectin and laminins. Described herein is unique approach to using placental tissue components in wound healing and other medical applications.

SUMMARY OF THE INVENTION

Described herein are tissue grafts composed of at least one membrane, where at least one side of that membrane additionally contains micronized placental tissue. Also described herein are methods for making and using the tissue grafts.

Several of the advantages of this invention are set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

FIGS. 9-12 are sometimes referred to as FIGS. 90-93, respectively.

DETAILED DESCRIPTION OF THE INVENTION

Before the present invention is disclosed and described, it is to be understood that the aspects described below are not limited to specific compositions, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a bioactive agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" as used herein is any vertebrate organism including but not limited to mammalian subjects such as humans, farm animals, domesticated pets and the like.

The term "amnion" as used herein includes amniotic membrane where the intermediate tissue layer is intact or has been substantially removed.

The term "exterior surface" refers to either or both surfaces of the tissue graft which will contact the tissue of the patient to which graft is applied.

The term "patient" refers to any and all mammals including, in particular, domesticated animals such as cows, horses, dogs, cats and sheep as well as primates including humans.

The term "placental tissue" refers to any and all of the well known components of the placenta including but not limited to amnion, chorion, Wharton's Jelly, and the like. In one preferred embodiment, the placental tissue does not include any of the umbilical cord components (e.g., Wharton's jelly, umbilical cord vein and artery, and surrounding membrane).

Titles or subtitles may be used in the specification for the convenience of a reader, which are not intended to influence the scope of the present invention. Additionally, some terms used in this specification are more specifically defined below.

Figure 1:
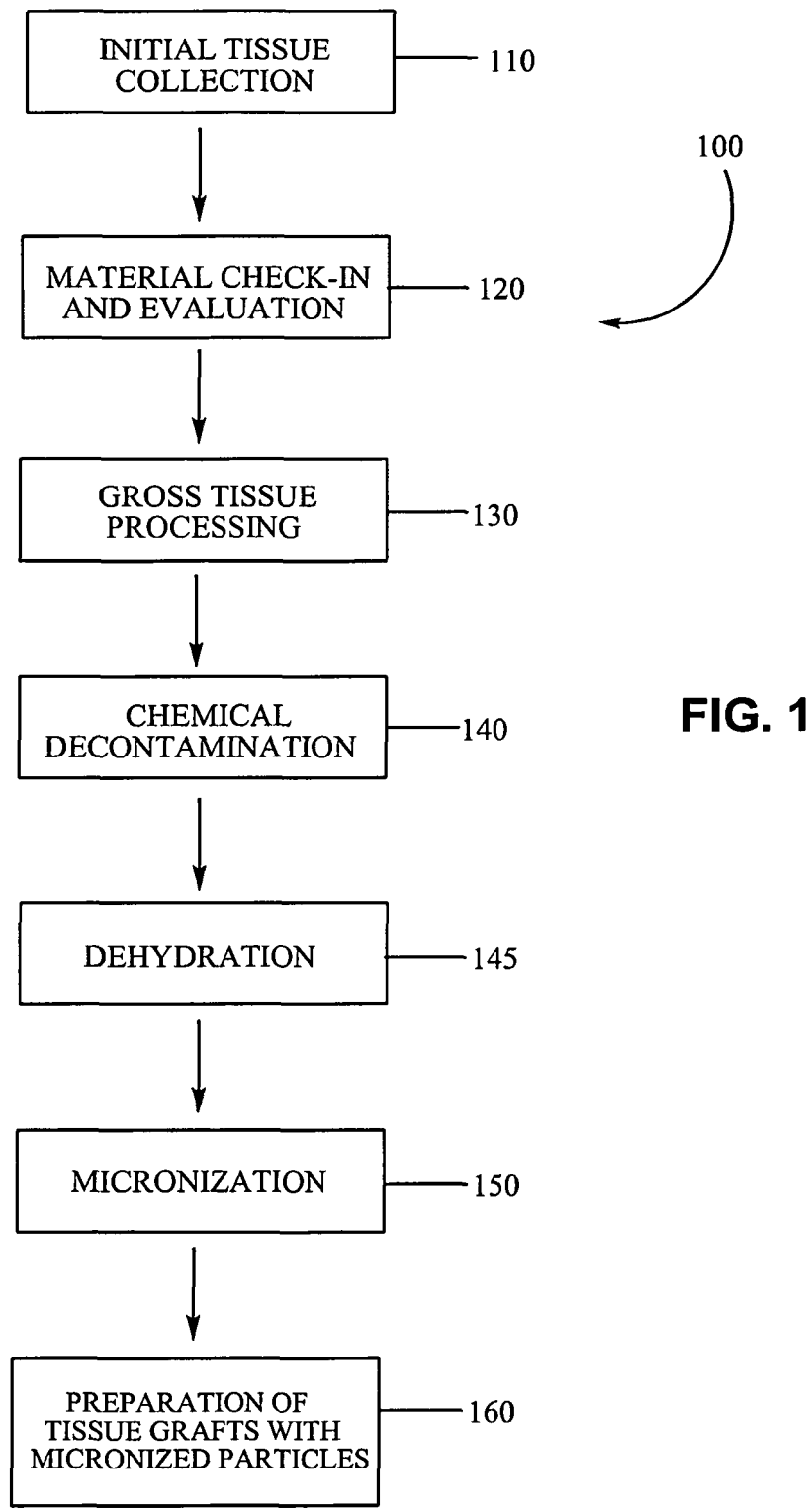
FIG. 1 is an overview flow chart of the process for making the tissue grafts composed of micronized placental tissue.

I. Tissue Grafts Composed of Micronized Placental Tissue and Methods for Making Thereof Described herein are tissue grafts composed of micronized placental tissue. FIG. 1 depicts an overview (100) and certain aspects of the steps to harvest, process, and prepare placental material for use in the preparation of the micronized placental tissue and tissue grafts described herein. More detailed descriptions and discussion regarding each individual step will follow. Initially, the placental tissue is collected from a consenting patient following an elective Cesarean surgery (step 110). The material is preserved and transported in conventional tissue preservation manner to a suitable processing location or facility for check-in and evaluation (step 120). Gross processing, handling, and separation of the tissue layers then takes place (step 130). Acceptable tissue is then decontaminated (step 140) and dehydrated (step 145). After decontamination dehydration, the placental tissue is then micronized (step 150). The micronized placental tissue is then applied to at least one side of a tissue graft (step 160). Each step is described in detail below.

Initial Tissue Collection (Step 110)

The components used to produce the micronized placental tissue and tissue grafts described herein are derived from the placenta. The source of the placenta can vary. In one aspect, the placenta is derived from a mammal such as human and other animals including, but not limited to, cows, pigs, and the like can be used herein. In the case of humans, the recovery of the placenta originates in a hospital, where it is preferably collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV) hepatitis B surface antigens (HBsAg), antibodies to the hepatitis C virus (anti-HCV), antibodies to the human T-lymphotropic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is exemplary only, as more, fewer, or different tests may be desired or necessary over time or based upon the intended use of the grafts, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta is collected prior to the completion of obtaining the results from the screening tests and delivery cultures, such tissue is labeled and kept in quarantine. The placenta is approved for further processing only after the required screening assessments and delivery cultures, which declare the tissue safe for handling and use, are satisfied and obtains final approval from a medical director.

Material Check-in and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing (Step 130)

When the tissue is ready to be processed further, the sterile supplies necessary for processing the placental tissue further are assembled in a staging area in a controlled environment and are prepared for introduction into a controlled environment. In one aspect, the placenta is processed at room temperature. If the controlled environment is a manufacturing hood, the sterile supplies are opened and placed into the hood using conventional sterilization techniques. If the controlled environment is a clean room, the sterile supplies are opened and placed on a cart covered by a sterile drape. All the work surfaces are covered by a piece of sterile drape using conventional sterilization techniques, and the sterile supplies and the processing equipment are placed onto the sterile drape, again using conventional sterilization techniques.

Processing equipment is decontaminated according to conventional and industry-approved decontamination procedures and then introduced into the controlled environment. The equipment is strategically placed within the controlled environment to minimize the chance for the equipment to come in proximity to or is inadvertently contaminated by the tissue specimen.

Next, the placenta is removed from the sterile shipment bag and transferred aseptically to a sterile processing basin within the controlled environment. The sterile basin contains hyperisotonic saline solution (e.g., 18% NaCl) that is at room or near room temperature. The placenta is gently massaged to help separate blood clots and to allow the placental tissue to reach room temperature, which facilitates the separation of the placental components from each other (e.g., amnion membrane and chorion). After having warmed up to ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the tissue is also noted. A determination is made, at this point, as to whether the tissue is acceptable for further processing.

The amnion and chorion are next carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion can be separated from the chorion. The amnion appears as a thin, opaque layer on the chorion.

The fibroblast layer is identified by gently contacting each side of the amnion with a piece of sterile gauze or a cotton tipped applicator. The fibroblast layer will stick to the test material. The amnion is placed into processing tray basement membrane layer down. Using a blunt instrument, a cell scraper, or sterile gauze, any residual blood is also removed. This step must be done with adequate care, again, so as not to tear the amnion. The cleaning of the amnion is complete once the amnion is smooth and opaque-white in appearance.

In certain aspects, the intermediate tissue layer, also referred to as the spongy layer, is substantially removed from the amnion in order to expose the fibroblast layer. The term "substantially removed" with respect to the amount of intermediate tissue layer removed is defined herein as removing greater than 90%, greater than 95%, or greater than 99% of the intermediate tissue layer from the amnion. This can be performed by peeling the intermediate tissue layer from the amnion. Alternatively, the intermediate tissue layer can be removed from the amnion by wiping the intermediate tissue layer with gauze or other suitable wipe. The resulting amnion can be subsequently decontaminated using the process described below.

In certain aspects, the epithelium layer present on the amnion is substantially removed in order to expose the basement layer of the amnion. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification.

The epithelium layer can be removed by techniques known in the art. For example, the epithelium layer can be scraped off of the amnion using a cell scraper.

Other techniques include, but are not limited to, freezing the membrane, physical removal using a cell scraper, or exposing the epithelial cells to nonionic detergents, anionic detergents, and nucleases. The de-epithelialized tissue is then evaluated to determine that the basement membrane has not been compromised and remains intact. This step is performed after completion of the processing step and the before the tissue has been dehydrated as described in the next section. For example, a representative sample graft is removed for microscopic analysis. The tissue sample is place onto a standard slide, stained with Eosin Y and viewed under the microscope. If epithelium is present, it will appear as cobblestone-shaped cells.

The methods described herein do not remove all cellular components in the amnion. This technique is referred to in the art as "decellularization." Decellularization generally involves the physical and/or chemical removal of all cells present in the amnion, which includes epithelial cells and fibroblast cells. For example, although the removal of epithelial cells is optional, the fibroblast layer present in the amnion stromal layer is intact, even if the intermediate tissue layer is removed. Here, fibroblast cells are present in the fibroblast layer.

Figure 2:
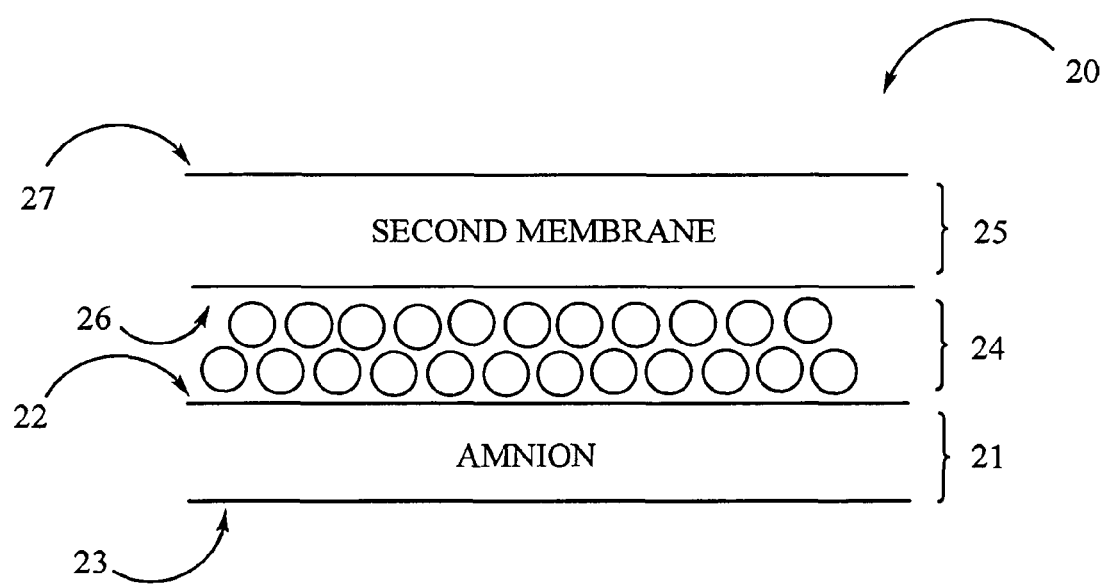
FIG. 2 depicts one embodiment of the tissue grafts described herein.

When the placental tissue is Wharton's jelly, the following exemplary procedure can be sued. Using a scalpel or scissors, the umbilical cord is dissected away from the chorionic disk. Once the veins and the artery have been identified, the cord is dissected lengthwise down one of the veins or the artery, as shown in FIG. 2. Once the umbilical cord has been dissected, surgical scissors and forceps can be used to dissect the vein and artery walls from the Wharton's jelly. Next, the outer layer of amnion is removed from the Wharton's jelly by cutting the amnion. Here, the outer membrane of the umbilical cord is removed such that Wharton's jelly is the only remaining component. Thus, the Wharton's jelly as used herein does not include the outer umbilical cord membrane and umbilical cord vessels. The Wharton's jelly can be cut into strips. In one aspect, the strips are approximately 1-4 cm by 10-30 cm with an approximate thickness of 1.25 cm; however, other thicknesses are possible depending on the application.

Chemical Decontamination (Step 140)

The amnion and chorion isolated above can be chemically decontaminated using the techniques described below. In one aspect, the amnion and chorion is decontaminated at room temperature. In one aspect, the amnion produced in step 130 (e.g., with or without the intermediate tissue layer) can be placed into a sterile Nalgene jar for the next step. In one aspect, the following procedure can be used to clean the amnion. A Nalgene jar is aseptically filled with 18% saline hypertonic solution and sealed (or sealed with a top). The jar is then placed on a rocker platform and agitated for between 30 and 90 minutes, which further cleans the amnion of contaminants. If the rocker platform was not in the critical environment (e.g., the manufacturing hood), the Nalgene jar is returned to the controlled/sterile environment and opened. Using sterile forceps or by aseptically decanting the contents, the amnion is gently removed from the Nalgene jar containing the 18% hyperisotonic saline solution and placed into an empty Nalgene jar. This empty Nalgene jar with the amnion is then aseptically filled with a premixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion. This jar or container containing the amnion and antibiotics is then sealed or closed and placed on a rocker platform and agitated for, preferably, between 60 and 90 minutes. Such rocking or agitation of the amnion within the antibiotic solution further cleans the tissue of contaminants and bacteria. Optionally, the amnion can be washed with a detergent. In one aspect, the amnion can be washed with 0.1 to 10%, 0.1 to 5%, 0.1 to 1%, or 0.5% Triton-X wash solution.

If the rocker platform was not in the critical environment (e.g., the manufacturing hood), the jar or container containing the amnion and antibiotics is then returned to the critical/sterile environment and opened. Using sterile forceps, the amnion is gently removed from the jar or container and placed in a sterile basin containing sterile water or normal saline (0.9% saline solution). The amnion is allowed to soak in place in the sterile water/normal saline solution for at least 10 to 15 minutes. The amnion may be slightly agitated to facilitate removal of the antibiotic solution and any other contaminants from the tissue. After at least 10 to 15 minutes, the amnion is ready to be dehydrated and processed further.

In the case of chorion, the following exemplary procedure can be used. After separation of the chorion from the amnion and removal of clotted blood from the fibrous layer, the chorion is rinsed in 18% saline solution for 15 minutes to 60 minutes. During the first rinse cycle, 18% saline is heated in a sterile container using a laboratory heating plate such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue was removed and placed into second heated agitation bath for an additional 15 minutes to 60 minutes rinse cycle. Optionally, the chorion tissue can be washed with a detergent (e.g., Triton-X wash solution) as discussed above for the decontamination of amnion. The container is sealed and agitated without heat for 15 minutes to 120 minutes. The chorion tissue is next washed with deionized water (250 ml of DI water×4) with vigorous motion for each rinse. The tissue is removed and placed into a container of 1×PBS w/EDTA solution. The container is sealed and agitated for 1 hour at controlled temperature for 8 hours. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

The following exemplary procedure can be used when the placental tissue is Wharton's jelly. The Wharton's jelly is transferred to a sterile Nalgene jar. Next, room temperature 18% hypertonic saline solution is added to rinse the tissue and the jar is sealed. The jar is agitated for 30 to 60 minutes. After incubation, the jar is decontaminated and returned to the sterile field. The tissue is transferred to a clean sterile Nalgene jar and prewarmed (about 48° C.) with 18% NaCl. The container is sealed and placed on rocker plate and agitated for 60 to 90 minutes.

After the rinse, the jar is decontaminated and returned to the sterile field. The tissue is removed and placed into an antibiotic solution. The container is sealed and agitated for 60 to 90 minutes on a rocker platform. Following incubation, the jar may be refrigerated at 1 to 10° C. for up to 24 hours.

The Wharton's jelly is next transferred to a sterile basin containing approximately 200 mL of sterile water. The tissue is rinsed for 1-2 minutes and transferred to a sterile Nalgene jar containing approximately 300 ml of sterile water. The jar is sealed and placed on the rocker for 30 to 60 minutes. After incubation, the jar is returned to the sterile field. The Wharton's jelly should have a cream white visual appearance with no evidence of brownish discoloration.

Dehydration (Step 145)

In one aspect, the placental tissue (e.g., amnion, chorion, intermediate tissue layer, Wharton's jelly) or any combination thereof can be processed into tissue grafts (i.e., laminates) that are subsequently micronized. In one aspect, the individual amnion, chorion, intermediate tissue layers can be dehydrated independently and subsequently micronized alone or as a mixture of components. In one aspect, the tissue (i.e., individual membrane or graft) is dehydrated by chemical dehydration followed by freeze-drying. In one aspect, the chemical dehydration step is performed by contacting the amnion, chorion, and/or intermediate layer with a polar organic solvent for a sufficient time and amount in order to substantially (i.e., greater than 90%, greater than 95%, or greater than 99%) or completely remove residual water present in the tissue (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the tissue can be freeze-dried directly as discussed below.

After chemical dehydration, the placental tissue is freeze-dried in order to remove any residual water and polar organic solvent. In one aspect, the placental tissue can be laid on a suitable drying fixture prior to freeze-drying. For example, one or more strips of amnion can be laid on a suitable drying fixture. Next, chorion is laid on top of the amnion. In this aspect, an amnion/chorion tissue graft is produced. Alternatively, a strip of amnion can be placed on a first drying fixture, and a strip of chorion can be placed on a second drying fixture. The drying fixture is preferably sized to be large enough to receive the placental tissue, fully, in laid out, flat fashion. In one aspect, the drying fixture is made of Teflon or of Delrin, which is the brand name for an acetal resin engineering plastic invented and sold by DuPont and which is also available commercially from Werner Machine, Inc. in Marietta, Ga. Any other suitable material that is heat and cut resistant, capable of being formed into an appropriate shape to receive wet tissue can also be used for the drying fixture.

Once the placental tissue is placed on the drying fixture, the drying fixture is placed in the freeze-dryer. The use of the freeze-dryer to dehydrate the tissue can be more efficient and thorough compared to other techniques such as thermal dehydration. In general, it is desirable to avoid ice crystal formation in the placental tissue as this may damage the extracellular matrix in the tissue. By chemically dehydrating the placental tissue prior to freeze-drying, this problem can be avoided.

In another aspect, the dehydration step involves applying heat to the placental tissue. In one aspect, the amnion, chorion, and/or intermediate layer is laid on a suitable drying fixture (either as individual strips or as a laminate discussed above), and the drying fixture is placed in a sterile Tyvex (or similar, breathable, heat-resistant, and sealable material) dehydration bag and sealed. The breathable dehydration bag prevents the tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into a non-vacuum oven or incubator that has been preheated to approximately 35 to 50 degrees Celcius. The Tyvex bag remains in the oven for between 30 to 120 minutes. In one aspect, the heating step can be performed at 45 minutes at a temperature of approximately 45 degrees Celcius to dry the tissue sufficiently but without over-drying or burning the tissue. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

In one aspect, the placental tissue grafts described herein can be dehydrated using an innovative dehydration device which enhances the rate and uniformity of the dehydration process. In one embodiment, the drying time can be accelerated by up to 40% in one configuration of the dehydration device in comparison to conventional drying ovens. In certain aspects, the placental tissue graft is placed onto a drying fixture described herein and the drying fixture with tissue graft is inserted into the dehydration device for performing the dehydration process. In other aspects, multiple placental tissue grafts can be placed onto the drying fixture to dry more than one placental tissue grafts in the dehydration device at the same time. Although the dehydration device is useful in dehydrating the tissue grafts described herein, they can be used for dehydrating objects other than placental tissue.

FIGS. 9-12 show an innovative dehydration device 900 according to an example embodiment that is well-suited for use in the herein-described dehydration processes. The dehydration device 900 includes a drying housing 902, and inflow plenum 904, and outflow plenum 906, an air-moving assembly 908, an air-heating assembly 910, and a control system 912.

Figure 9:
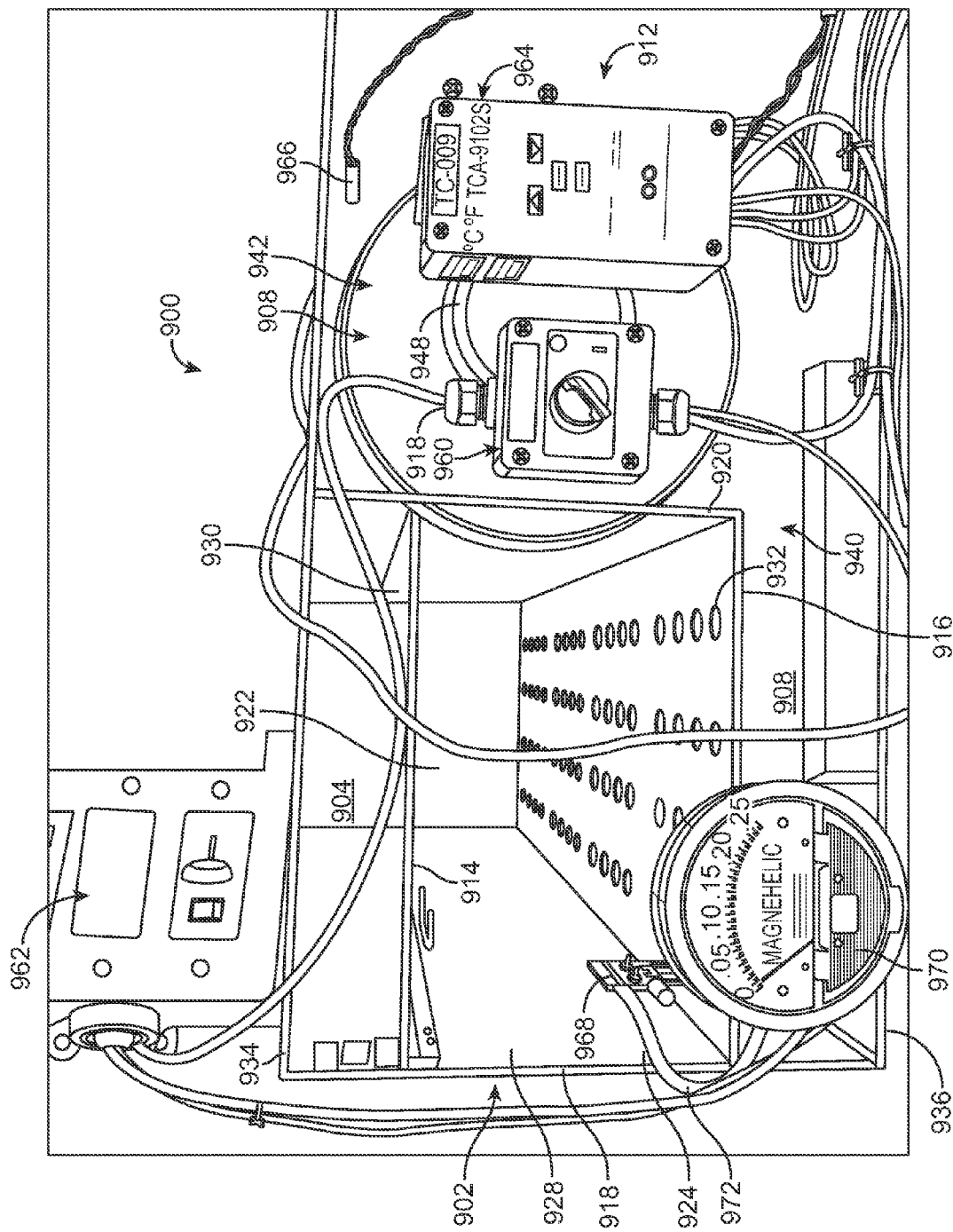
FIG. 9 shows a forward perspective view of a dehydration device as described herein.
Figure 10:
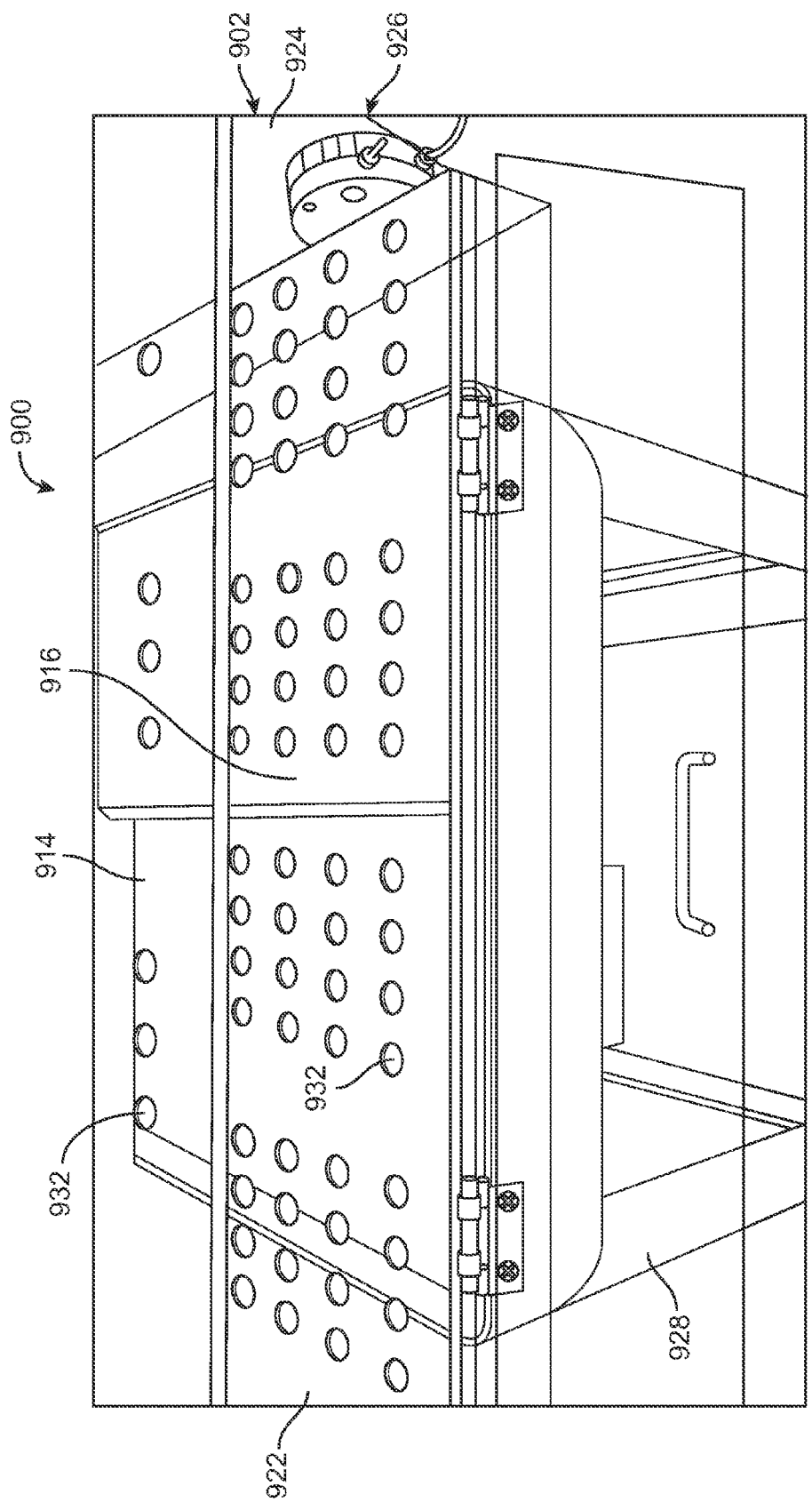
FIG. 10 shows an overhead perspective view of a dehydration device as described herein.
Figure 11:
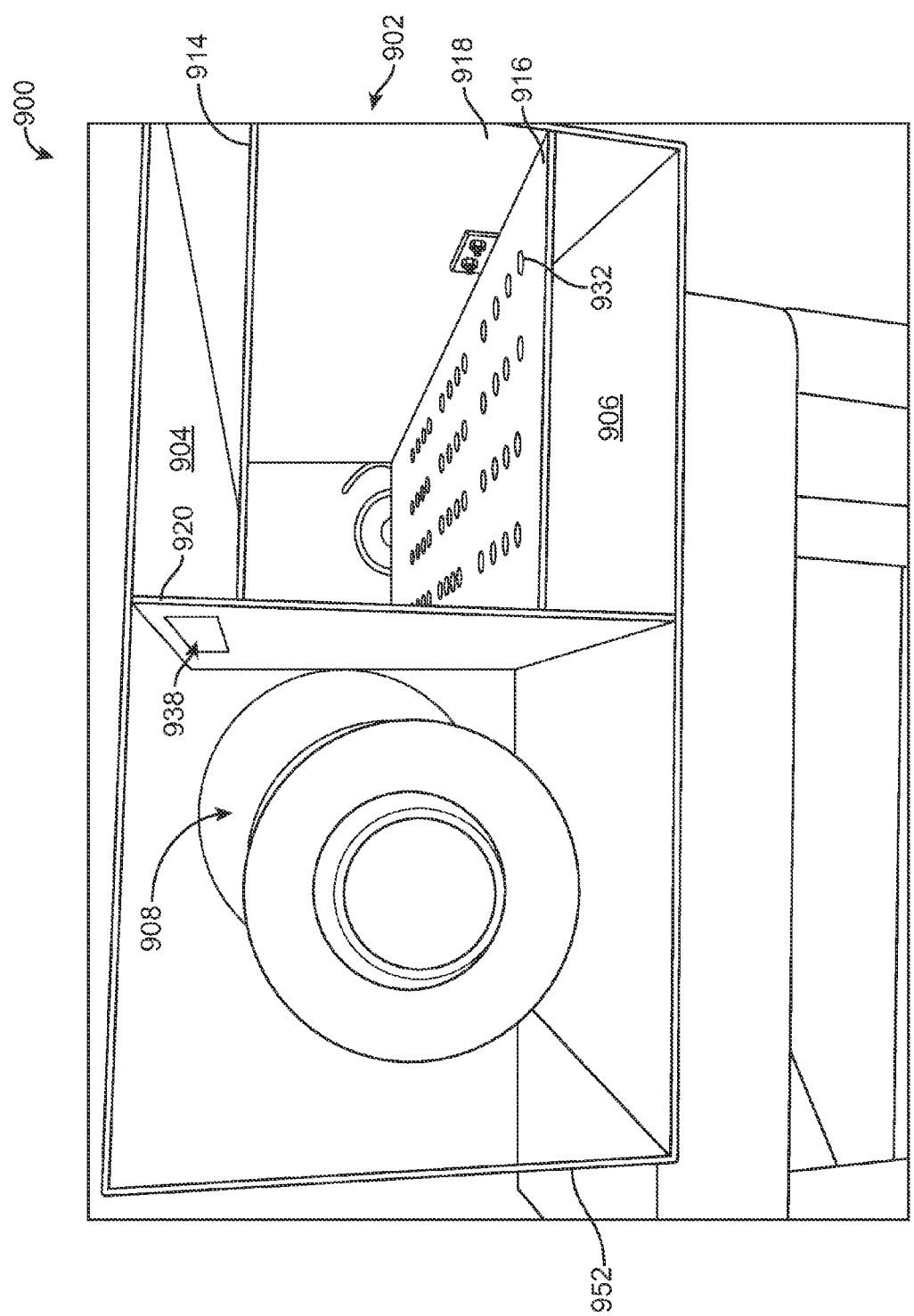
FIG. 11 shows a side perspective view of a dehydration device as described herein.
Figure 12:
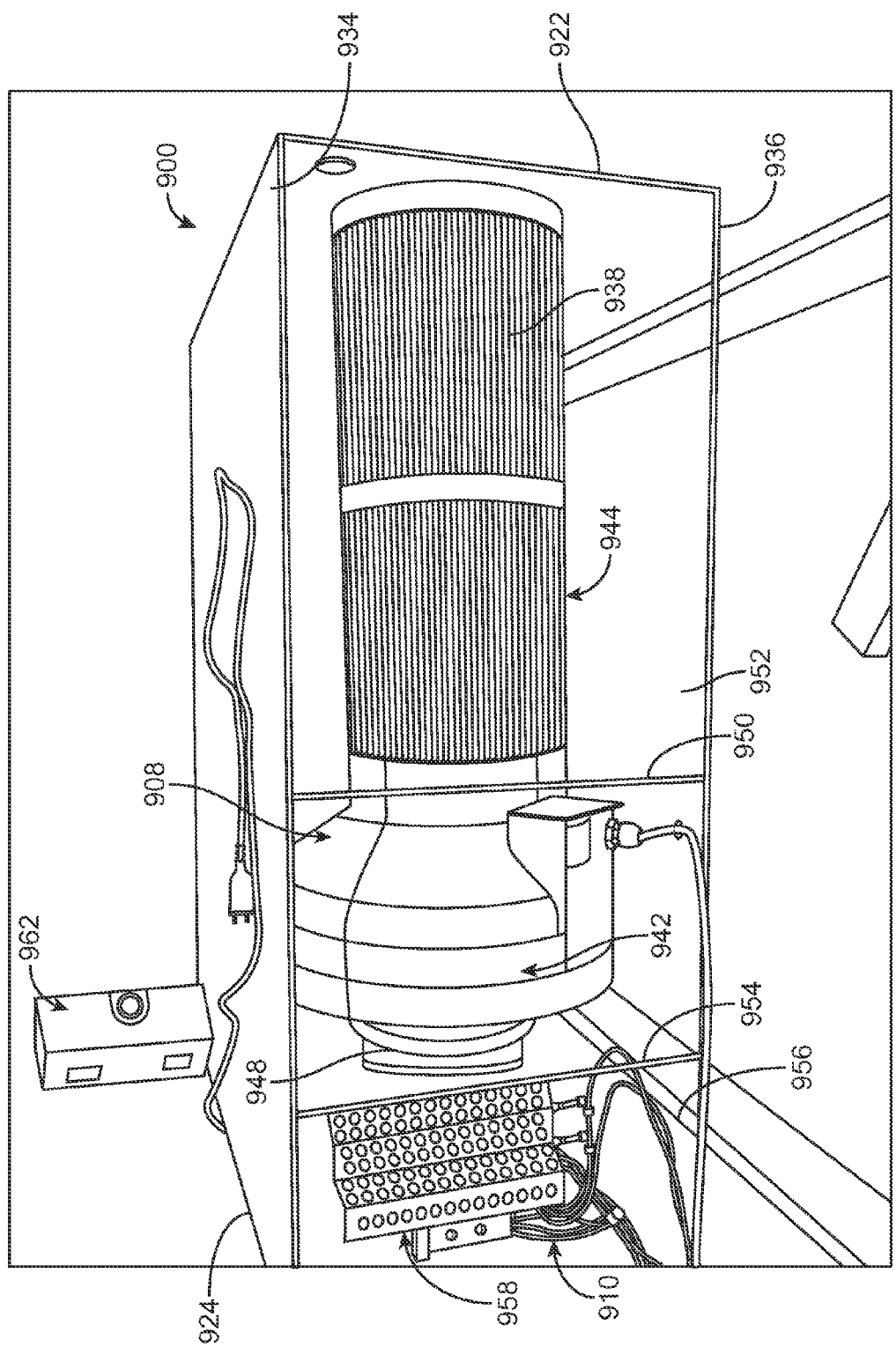
FIG. 12 shows a back perspective view of a dehydration device as described herein.

The drying housing 902 defines a drying chamber into which the placental tissue (e.g., ton a drying fixture) is placed for drying during the dehydration process. In typical embodiments, the drying housing 902 (and thus the drying chamber it defines) is formed by six generally planar walls arranged together in a generally rectanguloid shape. In other embodiments, the drying housing 902, and/or the drying chamber it defines, has a different regular or irregular shape such as spherical or ellipsoidal. In the depicted embodiment, the drying housing 902 is formed by top and bottom opposing walls 914 and 916, first and second opposing sidewalls 918 and 920, and first and second opposing endwalls 922 and 924. The drying housing 902 includes a doorway opening 926 and a door 928 (e.g. hingedly coupled to the housing and including a pull-knob) in at least one of the walls (e.g., sidewall 918) for inserting the placental tissue on a fixture for dehydration and then removing the dried tissue. (FIG. 9 shows the door 928 in a closed position and FIG. 10 shows it in an opened position.) The walls of the housing 902 are typically made of a material selected for rigidity, strength, and heat-resistance, for example an acrylic (e.g., PLEXIGLAS), glass, ceramic, or other polymeric material.

At least two of the walls of the housing 902 each define at least one respective aperture through which air can flow. In the depicted embodiment, for example, the top and bottom opposing walls 914 and 916 have an array of inflow and outflow apertures 930 and 932, respectively, formed in them. In such embodiments, the placental tissue graft (e.g., on a fixture) is placed into the drying chamber supported by the bottom wall 916 and typically at least partially covering at least one of the outflow apertures 932. The size, shape, and position of the apertures 930 and 932 are selected based on the range of operating parameters (volumetric flow rate, flow pattern, temperature, pressure, time/duration, etc. of the air flowing through the housing 902) of the device 900 as may be desired for drying the placental tissue. Thus, the apertures 930 and 932 can be circular, aligned with corresponding apertures in the opposing wall, arranged in segmented rows and/or columns, and arranged uniformly (for a generally uniform temperature and drying effect across the chamber), as depicted. In other embodiments, the apertures have a non-circular shape (e.g., polygonal or elliptical), have differing sizes (e.g., interspersed larger and smaller apertures, or differing inflow and outflow aperture sizes), and/or are formed in an irregular and/or non-aligning pattern. And in yet other embodiments, the apertures are formed in only one of the walls, more than two of the walls, or the opposing sidewalls 918 and 920 (instead of or in addition to the opposing top and bottom walls 914 and 916), and/or the inflow plenum 904 can be eliminated and piping coupled between the air-moving assembly 908 and an inflow one of the walls (e.g., top wall 914).

The inflow plenum 904 and the outflow plenum 906 are positioned in communication with the inflow apertures 930 and the outflow apertures 932, respectively. The plenums 904 and 906 help generate an even distribution of the pressure, flow, and temperature of the air flowing through the drying housing 902. In the depicted embodiment, the inflow plenum 904 is formed by first vertically upward extensions of the opposing sidewalls 918 and 920 and the opposing endwalls 922 and 924 together with the housing top wall 914 and an opposing inflow-plenum top wall 934. And the outflow plenum 906 is formed by second vertically downward extensions of the opposing sidewalls 918 and 920 and the opposing endwalls 922 and 924 together with the housing bottom wall 916 and an opposing outflow-plenum bottom wall 936. In other embodiments, the plenums 904 and 906 are eliminated and the air-moving assembly 908 is piped directly to the drying housing 902.

The inflow plenum 904 and the outflow plenum 906 include at least one inflow port 938 and outflow port 940, respectively. In the depicted embodiment, the inflow port 938 is defined by a generally rectangular opening formed in the sidewall 920 at an upper portion thereof and at a first/distal portion thereof, and the outflow port 940 is defined by a generally rectangular gap in the same sidewall (i.e., an absence of the second extension of the wall) but at a lower portion thereof and at a second/proximal portion thereof. In this way, the air flows laterally into the inflow plenum 904 at the first/distal and upper portion of the dehydration device 900 and then distributes proximally within the inflow plenum. Then the air flows down through the inflow apertures 930, down through and across the drying chamber, down through the outflow apertures 932, down into the outflow plenum 906, and laterally out at the second/proximal and lower portion of the device 900. The plenums 904 and 906 provide for generally evenly distributed airflow across the tissue even though the air enters the inflow plenum at the first/distal portion of the dehydration device 900 and exits the outflow plenum at the second/proximal portion (while flowing from top to bottom through the drying chamber). Alternatively, the inflow and outflow ports 938 and 940 can be positioned to provide airflow from bottom to top (and/or from side to side) through the drying chamber, and/or they can have other regular or irregular shapes such as circular.

The air-moving assembly 908 can be of a commercially available type for use in sterile/clean-air environments such as medical laboratories. Typically, the air-moving assembly 908 includes a blower 942 and a filter 944. The blower 942 can be of a conventional type, for example including an electric motor and a fan enclosed within a housing. And the filter 944 can be of a conventional type, for example a cylindrical HEPA air filter with an internal bore. Typically, such filter 944 mounts to and extends from the blower 942, and air flows axially through the internal bore and radially outward through the filter media.

The dehydration device 900 can be configured in a closed airflow loop (to re-circulate the air) or in an open loop (to provide fresh intake air). In closed-loop designs, an air outlet surface 946 of the filter 944 is in sealed communication with the inflow port 938 of the inflow plenum 904, and an air intake 948 of the blower 942 is in sealed communication with the outflow port 940 of the outflow plenum 906. In the depicted embodiment, for example, the air outlet surface 946 of the filter 944 is enclosed in a first/distal delivery chamber formed by lateral extensions of the plenum top and bottom walls 934 and 936, a lateral extension of the first/distal endwall 922 and an opposing second/proximal delivery-chamber endwall 950, and the second sidewall 920 and an opposing delivery-chamber sidewall 952. And the air intake 948 of the blower 942 is sealed communication with a second/proximal return chamber formed by lateral extensions of the plenum top and bottom walls 934 and 936, a lateral extension of the second/proximal endwall 924 and an opposing first/distal return-chamber endwall 954 (having an return opening in sealed communication with the blower air intake), and the second sidewall 920 and an opposing return-chamber sidewall 956. A sidewall section can be provided to enclose the blower 942 or this can be left out to allow ambient air exposure to prevent the blower from overheating. In the depicted embodiments, the result is that the outer walls of the dehydration device 900 form a rectanguloid structure. In other embodiments, the air outlet surface 946 of the filter 944 is piped to the inflow port 938 of the inflow plenum 904 and the air intake 948 of the blower 942 is piped to the outflow port 940 of the outflow plenum 906.

The air-heating assembly 910 includes at least one heating element 958, which can be of a conventional type such as a commercially available electric-resistance heating element. The heating element 958 is typically positioned adjacent the air intake 948 of the blower 942, for example mounted on a bracket within the return chamber, as depicted.

The control system 912 includes conventional controls for controlling the operating parameters (airflow rate, pressure, temperature, time/duration, etc.) of the dehydration device 900. Such conventional controls typically include a main power switch 960 that is wired to provide power to a variable resistance device 962 and a control unit 964. The main power switch 960 is wired to a power source such as conventional 120/240 line voltage. The variable resistance device 962 (e.g., a rheostat) is wired (for power and control) to the heating element 958 (e.g., via the control unit 964) for temperature control. At least one heat sensor 966 is positioned in the return chamber and wired to the control unit 964 to provide an input for use in temperature control. And the control unit 964 is wired (for power and control) to the blower 942 for controlling the volume flow rate (and thus also the pressure) and the time/duration of the dehydration cycle. In addition, typical embodiments such as that depicted include a pressure sensor 968 in (or at least exposed to) the drying chamber, a pressure gauge display 970 (e.g., mounted to the drying housing 902), and a fluid connection 972 (e.g., tubing) interconnecting the two parts.

Preparation of Micronized Placental Tissue (Step 150)

Once the placental tissue has been dehydrated individually or in the form a of tissue graft, the dehydrated tissue(s) is micronized. The micronized compositions can be produced using instruments known in the art. For example, the Retsch Oscillating Mill MM400 can be used to produce the micronized compositions described herein. The particle size of the materials in the micronized composition can vary as well depending upon the application of the micronized composition. In one aspect, the micronized composition has particles that are less than 500 µm, less than 400 µm, less than 300 µm, less than 200 µm, less than 100 µm, less than 50 µm, less than 25 µm, less than 20 µm, less than 15 µm, less than 10 µm, less than 9 µm, less than 8 µm, less than 7 µm, less than 6 µm, less than 5 µm, less than 4 µm, less than 3 µm, less than 2 µm, or from 2 µm, to 400 µm, from 25 µm to 300 µm, from 25 µm to 200 µm, or from 25 µm to 150 µm. In one aspect, the micronized composition has particles that have a diameter less than 150 µm, less than 100 µm, or less than 50 µm. In certain aspects, particles having a larger diameter (e.g. 150 µm to 350 µm) are desirable. In all cases, the diameter of the particle is measured along its longest axis.

In one embodiment, the size of the particles may be reduced to nano-range. As one skilled in the art would understand, nanoparticles of placental components may be desirable for the increased density and/or increased release rate upon applying to the wound. Preferably, the particle size of the micronized particles is from about 0.05 µm to about 2 µm, from about 0.1 µm to about 1.0 µm, from about 0.2 µm to about 0.8 µm, from about 0.3 µm to about 0.7 µm, or from about 0.4 µm to about 0.6 µm. Alternatively, the particle size of the micronized particles is at least 0.05 µm, at least 0.1 µm, at least 0.2 µm, at least 0.3 µm, at least 0.4 µm, at least 0.5 µm, at least 0.6 µm, at least 0.7 µm, at least 0.8 µm, at least 0.9 µm, or at least 1 µm. Alternatively, the particle size of the micronized particles is less than 1 µm, less than 0.9 µm, less than 0.8 µm, less than 0.7 µm, less than 0.6 µm, less than 0.5 µm, less than 0.4 µm, less than 0.3 µm, less than 0.2 µm, less than 0.1 µm, or less than 0.05 µm.

In other aspects, particles having a range of sizes and volumes are preferred as such particles will impart differential release rates into the wound. In one embodiment, particles having a range of mass to volume ratios can be prepared by either micronizing a mixture of a monolayer graft with multi-layer grafts (e.g., 2-10 layers) such that a range of graft sizes and volumes are provided. In another embodiment, particles of varying surface area to volume ratios of the same tissue material can be prepared by compressing the linear grafts into balls of varying sizes and shapes (round, elliptical, oblong, etc.). As the volume to surface area ratio is increased, particle dissipation increases due to the larger exposure area for endogenous enzymes, etc. This results in a faster rate of release of collagen types IV, V, and VII, cell-adhesion bio-active factors including fibronectin and laminins and other components of the micronized particles. On the other hand, as the surface area to volume ratio is decreased, particle dissipation decreases due to the smaller exposure area for endogenous enzymes, etc. This results in a slower rate of release of collagen types IV, V, and VII, cell-adhesion bio-active factors including fibronectin and laminins and other components of the micronized particles. In combination, the use of a layer of micronized particles having different surface area to volume ratios provides for a "time-release" mechanism whereby the benefits of the micronized graft are both immediate and prolonged.

In one embodiment, the surface area to volume ratio (based on a sphere using the ranges for the diameter set forth above) is between the range of about 0.06 µm to about $6 \times 10^4$ µm, about 0.06 µm to about $6 \times 10^3$ µm, about 0.06 µm to about $6 \times 10^2$ µm, or about 0.6 µm to about $6 \times 10^2$ µm.

In one aspect, the initial micronization is performed by mechanical grinding or shredding. In another aspect, micronization is performed cryogenic grinding. In this aspect, the grinding jar containing the tissue is continually cooled with liquid nitrogen from the integrated cooling system before and during the grinding process. Thus, the sample is embrittled and volatile components are preserved. Moreover, the denaturing of proteins in the amnion, intermediate tissue layer, and/or chorion is minimized or prevented. In one aspect, the CryoMill manufactured by Retsch can be used in this aspect.

On the other hand, one skilled in the art would appreciate that the particle size of the micronized placental components can be reduced to nano-range, thereby significantly increasing the density of the micronized particles and improving the release rate of the micronized particles upon application to wounds or other treatment sites. For example, the micronized placental components can be subjected to conventional methods known in the art, including differential centrifugation, thereby reducing the particle size to nano-range. Particle size reduction using a suitable technology or device is within the purview of one skilled in the art. In one embodiment, the micronized particles can be embedded into the surface of the amnion or chorion which is to contact the tissue surface. Conventional technology such as high velocity sprayer can result in surface loading of the micronized particles so as to result in enhanced release rates of growth factors and the like into the tissue.

The selection of the placental tissue used to make the micronized components described herein can vary depending upon the end-use of the composition. For example, amnion, chorion, intermediate tissue layer, or any combination thereof as individual components can be admixed with one another and subsequently micronized. In another aspect, one or more tissue grafts composed of one or more amnion, chorion, intermediate tissue layers, or any combination thereof (i.e., laminates) can be micronized. In a further aspect, one or more tissue grafts composed of one or more amnion, chorion, intermediate tissue layers, or any combination can be admixed with amnion, chorion, intermediate tissue layer, or any combination thereof as individual components and subsequently micronized.

The amount of different placental tissue components used to make the micronized compositions described herein can vary depending upon the application of the micronized composition. In one aspect, when the micronized composition is composed of amnion (with or without the intermediate tissue layer) and intermediate tissue layer, the weight ratio of amnion to intermediate tissue layer is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1. In another aspect, when the micronized composition is composed of amnion (with or without the intermediate tissue layer) and chorion, the weight ratio of chorion to amnion is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1.

In one aspect, separation of particle sizes can be achieved by fractionation of the micronized material in sterile water by forming a suspension of particles. In this aspect, the upper most portion of the suspension will contain predominantly the smallest particles and the lower most portion of the suspension will contain predominantly the heaviest particles. Fractionation leads to particle size separation and repeated fractionation will lead to separation of the micronized particles into varying sizes. The separated particles can be recombined in the desired ratio of particle size as is most appropriate for the wound to be treated.

In addition to the placental tissue, additional components can be added to the composition prior to and/or after micronization. In one aspect, a filler can be added. Examples of fillers include, but are not limited to, allograft pericardium, allograft acellular dermis, purified xenograft Type-1 collagen, biocellulose polymers or copolymers, biocompatible synthetic polymer or copolymer films, purified small intestinal submucosa, bladder acellular matrix, cadaveric fascia, or any combination thereof.

In another aspect, a bioactive agent can be added to the composition prior to and/or after micronization. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon application of the micronized composition with bioactive agent to the region of interest, the bioactive agent is delivered to the region over time. Thus, the micronized particles described herein are useful as delivery devices of bioactive agents and other pharmaceutical agents when administered to a subject. Release profiles can be modified based on, among other things, the selection of the components used to make the micronized compositions as well as the size of the particles.

In a further aspect, the amnion can be cross-linked with the intermediate tissue layer, chorion, or a second amnion tissue. For example, a cross-linking agent can be added to the placental tissue components (e.g., amnion, chorion, intermediate tissue layer, or any combination thereof as individual components and/or as tissue grafts) prior to and/or after micronization. In general, the cross-linking agent is nontoxic and non-immunogenic. When the placental tissue components (e.g., amnion, intermediate tissue layer, and/or chorion or a tissue graft thereof) are treated with the cross-linking agent, the cross-linking agent can be the same or different. In one aspect, the amnion, intermediate tissue layer, and chorion can be treated separately with a cross-linking agent or, in the alternative, the amnion, intermediate tissue layer, and chorion can be treated together with the same cross-linking agent. In certain aspects, the amnion, intermediate tissue layer, and chorion can be treated with two or more different cross-linking agents. The conditions for treating the amnion, intermediate tissue layer, and chorion can vary. In other aspects, the amnion, intermediate tissue layer, and/or chorion can be micronized, and the micronized composition can subsequently be treated with a cross-linking agent. In one aspect, the concentration of the cross-linking agent is from 0.1 M to 5 M, 0.1 M to 4 M, 0.1 M to 3 M, 0.1 M to 2 M, or 0.1 M to 1 M. In another aspect, the amnion or chorion are treated with the cross-linking agent for 1 to 2 seconds up to 60 minutes. In a further aspect, the amnion or chorion are treated with the cross-linking agent at room temperature up to 50° C.

The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehyde such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy] succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, disuccinimidyl suberate, and 1-ethyl-3-[3-dimethylaminopropyl]carbodiimide hydrochloride, a bifunctional oxirane (OXR), or ethylene glycol diglycidyl ether (EGDE).

In one aspect, sugar is the cross-linking agent, where the sugar can react with proteins present in the placental tissue to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as a cross-linking agent include, but are not limited to, D-ribose, glycerose, altrose, talose, ertheose, glucose, lyxose, mannose, xylose, gulose, arabinose, idose, allose, galactose, maltose, lactose, sucrose, cellibiose, gentibiose, melibiose, turanose, trehalose, isomaltose, or any combination thereof. Thus, in one aspect, the amnion or chorion include at least one cross-linker covalently attached to the membrane. In another aspect, a tissue graft includes an amnion and a chorion laminate, wherein the amnion and chorion are covalently attached to one another via a cross-linker.

Preparation of Tissue Grafts with Micronized Placental Tissue (Step 160)

Any of the micronized placental components described herein can be applied to the surface of a membrane to produce new tissue grafts for wound healing and other medical applications. The membranes useful herein can be any placental tissue described herein (e.g., amnion, chorion, intermediate layer, Wharton's jelly, or any combination thereof in the form of a laminate). In certain aspects, the membrane and the micronized particles are composed of the same placental components. In other aspects, the membrane and the micronized particles are composed of different placental components.

In one aspect, the biocompatible mesh as described herein can be either structurally homologous or heterologous in its configuration, wherein a structurally homologous biocompatible mesh is wholly composed from placental tissue, including, but not limited to, be amnion, chorion, Wharton's jelly and the like, and wherein a structurally heterologous biocompatible mesh is composed from placental tissue that can be any combination of placental tissues as described herein.

The micronized placental tissue is applied to at least one side of the membrane using a number of techniques. In one aspect, the micronized placental tissue can be applied to the surface of the membrane as a dry powder. In this aspect, the micronized placental tissue can be sprinkled on the surface of the membrane. In certain aspects, the micronized placental tissue can be applied directly to the surface of the membrane without the use of glues or adhesives. For example, when the membrane is amnion with an exposed fibroblast layer, the exposed fibroblast layer can act as an adhesive and bind the micronized placental tissue to the membrane without using an adhesive. In other aspects, adhesives such as fibrin glue can be used to adhere the micronized placental tissue to the surface of the membrane.

In another aspect, the micronized placental tissue may be applied to the surface of the membrane by first depositing the micronized placental tissue onto a non-stick surface such as Teflon® and subsequently thereafter contacting one or both surfaces of the membrane with the deposited micronized placental tissue to absorb the micronized placental tissue onto the interior surface of the membrane. In this aspect, the non-stick surface can be sterilized according to conventional methods, such as the steps of heating, drying and cooling down, prior to deposition of the micronized placental tissue. In certain aspects, the membrane can be provided in a wet form to facilitate adhesion of the micronized placental tissue to the membrane. In another aspect, a second membrane can be later applied onto the first membrane containing the micronized placental tissue to produce a tissue graft.

In other aspects, the micronized placental tissue can be formulated in an excipient the biological system or entity can tolerate prior to applying the micronized placental tissue to the surface of the membrane. Examples of such excipients include, but are not limited to, water, aqueous hyaluronic acid, saline, Ringer's solution, dextrose solution, Hank's solution, and other aqueous physiologically balanced salt solutions. Here, the formulation composed of the micronized placental tissue can be applied to the surface of the membrane by coating or spraying the formulation on the membrane surface. The coated membrane can be subsequently dehydrated using the techniques described above.

In another aspect, the micronized placental tissue can be injected into a tissue graft or applied directly to a wound site as a jetted solution using a needle-free transdermal transport device. Jetting techniques using needle-free transdermal transport devices are known by those of skill in the art. In certain aspects, jetting techniques may be used as a substitute method for applying micronized placental tissue. Alternatively, jetting techniques may be used to supplement additional micronized placental tissue to the tissue graft or wound site to enhance wound healing and other medical applications. In certain other aspects, the micronized placental tissue may be provided in any suitable medium depending on the jetting technique being used, including, but not limited to, solutions, suspensions and powders.

It will be appreciated that the actual preferred amounts of micronized placental tissue used to prepare the tissue grafts described herein in a specified case will vary according to the specific compound being utilized, the particular compositions formulated, the mode of application, and the particular situs and subject being treated. Dosages for a given host can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999).

FIGS. 2-8 depict exemplary tissue grafts described herein.

FIG. 2 depicts a tissue graft 20 comprising:
 a first membrane comprising amnion 21, wherein the first membrane has a first side 22 and a second side 23;
 a first layer of micronized placental tissue 24 adjacent to the first side of the first membrane; and
 a second membrane 25 having a first side 26 and second side 27, wherein the first side of the second membrane is adjacent to the first layer of micronized placental tissue.

In this aspect, the micronized placental tissue is sandwiched between the first and second membrane. In one aspect, the first membrane comprises modified amnion wherein the modified amnion comprises a first side having an exposed fibroblast layer. In this aspect, the intermediate layer of the amnion has been removed, where the amnion has an intact epithelial layer. In another aspect, the first membrane comprises modified amnion wherein the modified amnion comprises a second side having an exposed basement membrane and a first side having an exposed fibroblast layer. In this aspect, the intermediate layer and the epithelium layer of the amnion have been removed. In a further aspect, the first membrane comprises amnion wherein the amnion comprises a first side having an intermediate layer and the second side has an epithelium layer.

Figure 3:
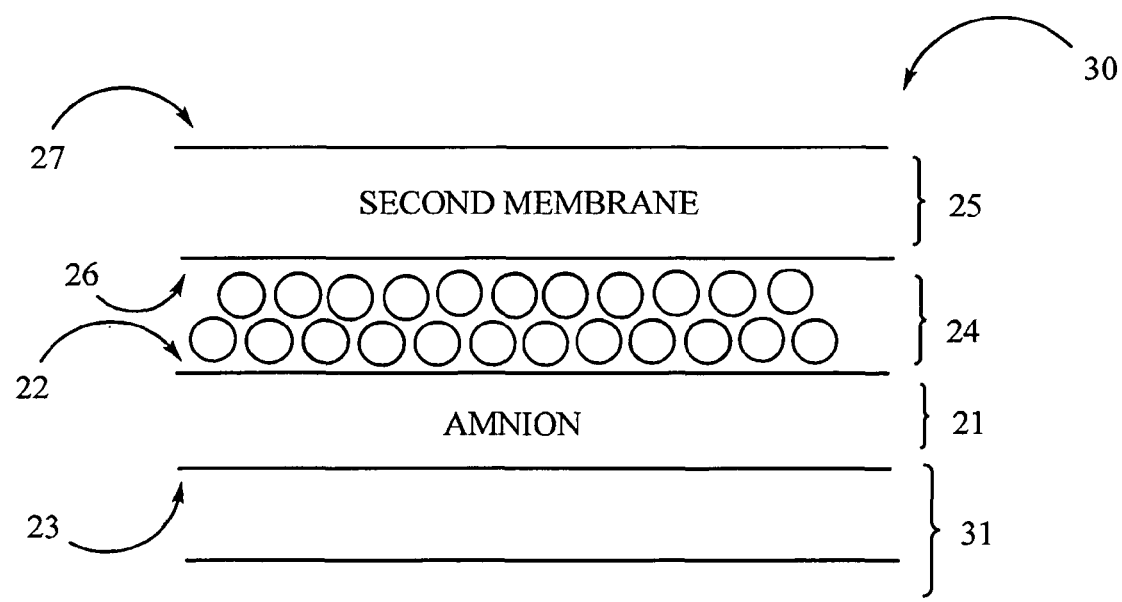
FIG. 3 depicts another embodiment of the tissue grafts described herein.

In another aspect, the first membrane comprises one or more additional membranes sequentially layered on the second side of the first membrane. This is depicted in FIG. 3, where the tissue graft 30 has one or more additional layers 31 adjacent to the second side 22 of the amnion. In one aspect, the one or more additional membranes comprises amnion, chorion, or a combination thereof. In another aspect, the one or more additional membranes comprises two or more amnion membranes sequentially layered to the second side of the first membrane.

In one aspect, the second membrane as described herein and depicted in FIGS. 2, 3, and 5-7 is amnion. In another aspect, the second membrane comprises modified amnion wherein the modified amnion comprises a first side having an exposed fibroblast layer, wherein the first side of the second membrane is adjacent to the first layer of micronized placental tissue. In another aspect, the second membrane comprises modified amnion wherein the modified amnion comprises a second side having an exposed basement membrane and a first side having an exposed fibroblast layer, wherein the first side of the second membrane is adjacent to the first layer of micronized placental tissue. In another aspect, the second membrane comprises amnion wherein the amnion comprises a first side having an intermediate layer, wherein the first side of the second membrane is adjacent to the first layer of micronized placental tissue.

Figure 4:
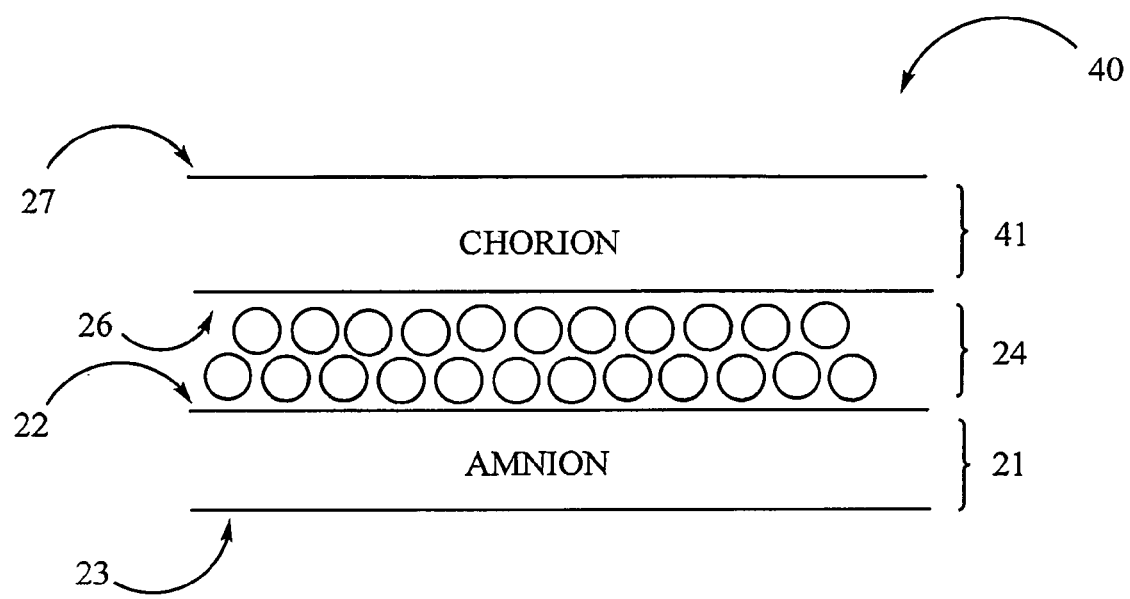
FIG. 4 depicts an alternative embodiment of the tissue grafts described herein.

In one aspect, the second membrane is chorion. This aspect is depicted in FIG. 4. The tissue graft 40 has chorion 41 adjacent to the micronized placental tissue 24. The chorion is composed of four layers: the cellular layer, the reticular layer, the pseudo-basement membrane, and the trophoblast. In one aspect, the cellular layer of the chorion is adjacent to the micronized placental tissue (i.e., first side 26 in FIG. 4). In another aspect, the trophoblast of the chorion is adjacent to the micronized placental tissue. As is apparent, the layer of placental tissue can be applied to either or both sides of the amnion or chorion.

Figure 5:
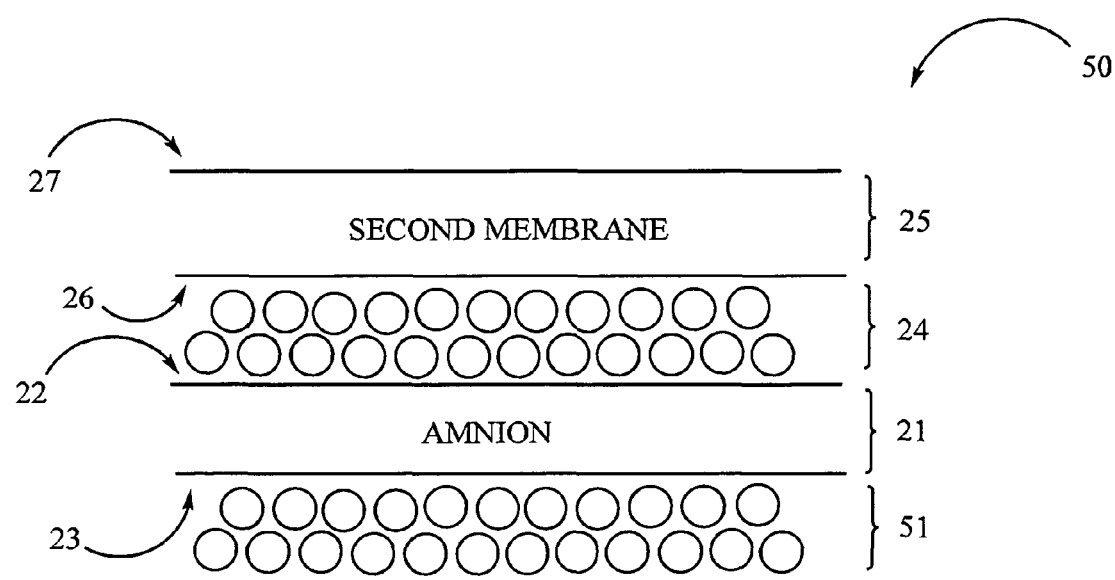
FIG. 5 depicts another embodiment of the tissue grafts described herein.
Figure 6:
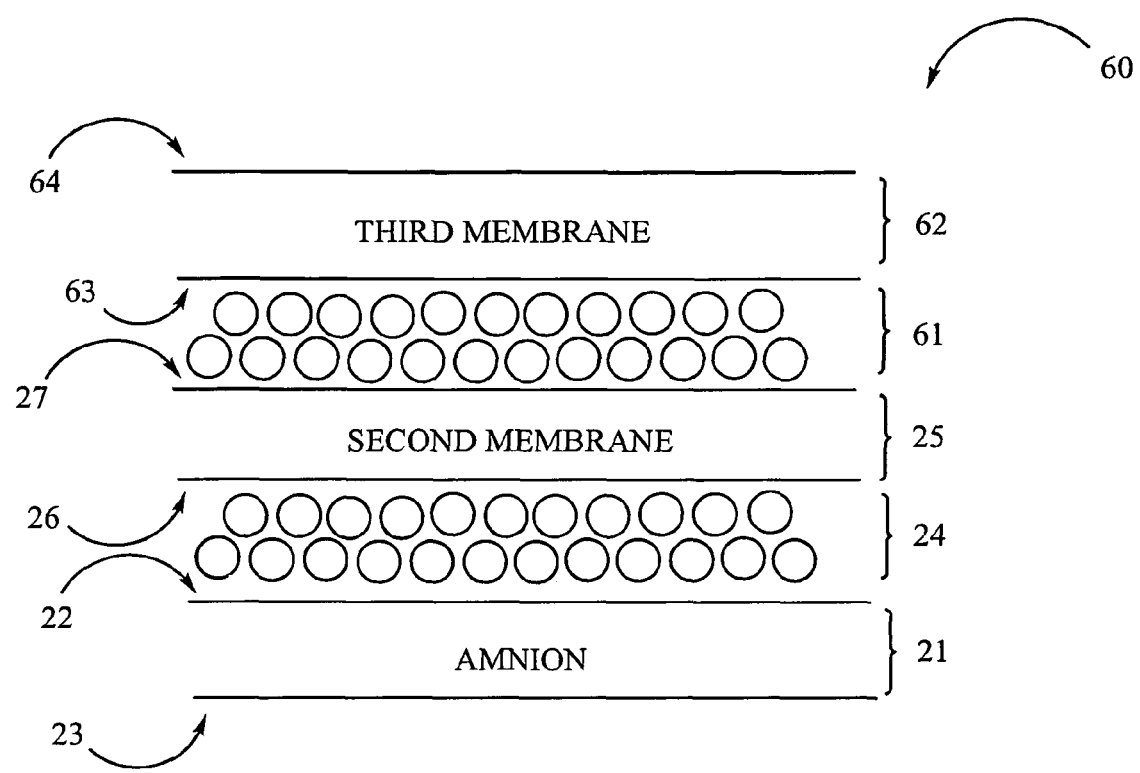
FIG. 6 depicts an alternative embodiment of the tissue grafts described herein.

In certain aspects, the tissue grafts described herein can have two or more layers of micronized placental tissue. An example of this is depicted in FIGS. 5 and 6. Referring to FIG. 5, the tissue graft 50 has a second layer of micronized placental tissue 51 that is adjacent to the second side 23 of amnion 21. Referring to FIG. 6, the tissue graft 60 comprises:
a second layer of micronized placental tissue 61 adjacent to the second side 27 of the second membrane 25; and
a third membrane 62 having a first side 63 and second side 64, wherein the first side of the third membrane is adjacent to the second layer micronized placental tissue.

Figure 7:
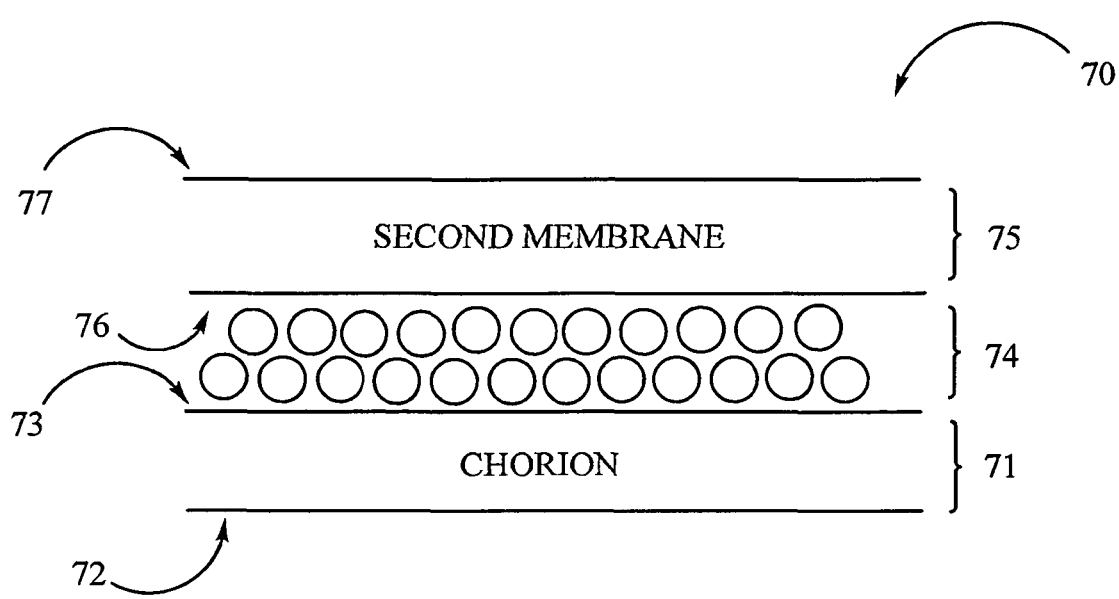
FIG. 7 depicts another embodiment of the tissue grafts described herein.

In another aspect, the tissue grafts do not include amnion membrane. An example of this is depicted in FIG. 7. In this aspect, the tissue graft 70 comprises:
a first membrane comprising chorion 71, wherein the first membrane has a first side 73 and a second side 72;
a first layer of micronized placental tissue 74 adjacent to the first side 73 of the first membrane 71; and
a second membrane 75 having a first side 76 and second side 77, wherein the first side of the second membrane is adjacent to the first layer of micronized placental tissue, and the second membrane is not amnion. In one aspect, the second membrane is chorion, intermediate layer or a laminate thereof. In another aspect, the second membrane is laminate composed of two or more chorion membranes. In one aspect, the cellular layer of the chorion is adjacent to the micronized placental tissue (i.e., first side 73 in FIG. 7). In another aspect, the trophoblast of the chorion is adjacent to the micronized placental tissue. Similarly, when the second membrane is chorion, the cellular layer or the trophoblast can be adjacent to the micronized placental tissue layer 74.

Figure 8:
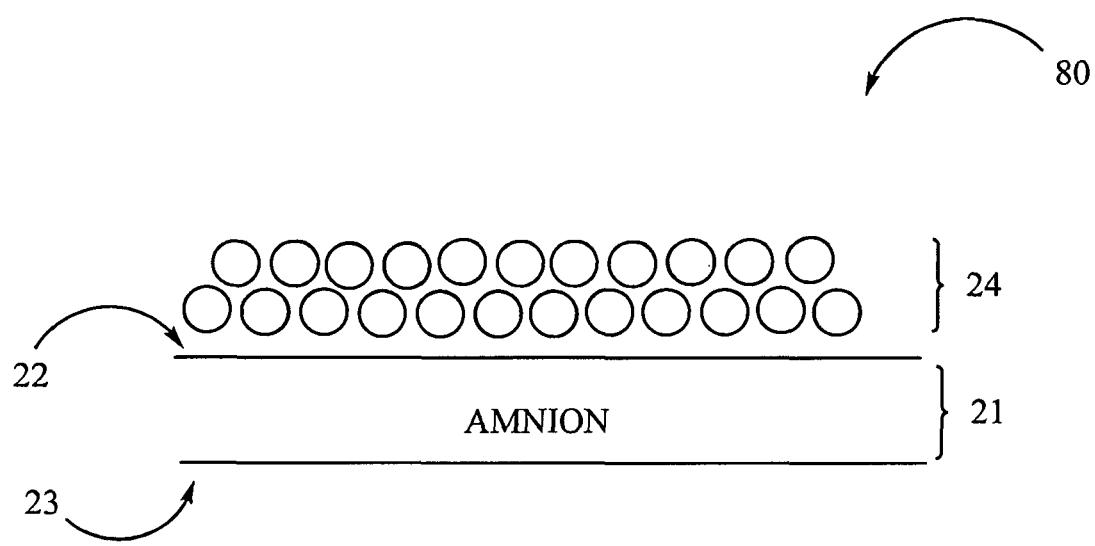
FIG. 8 depicts another embodiment of the tissue grafts described herein.

In other aspect, the micronized placental tissue can be applied to a membrane, where the tissue graft is not configured as a sandwich. An example of this is depicted in FIG. 8. Here, the tissue graft 80 comprises:
a first membrane comprising amnion 21, wherein the first membrane has a first side 22 and a second side 23; and
a first layer of micronized placental tissue 24 adjacent to the first side of the first membrane.

In one aspect, the tissue graft is depicted in FIG. 4, where the first side 22 of the amnion 21 has an exposed fibroblast layer, and the micronized placental tissue is one of the following:
1. micronized amnion and intermediate tissue layer as individual components, wherein the intermediate tissue layer has been removed from the amnion;
2. a micronized tissue graft comprising at least two layers of chorion, at least two layers of amnion membrane, or at least one layer of chorion and amnion membrane;
3. a micronized amnion/chorion tissue graft;
4. a micronized tissue graft comprising:
   a first membrane comprising modified amnion wherein the modified amnion comprises a first side and a second side comprising an exposed fibroblast layer, wherein the amnion is not decellularized; and
   one or more additional membranes sequentially layered such that the first additional membrane is layered adjacent to the exposed fibroblast layer,
   wherein the at least one or more additional membranes comprises amnion, chorion, allograft pericardium, allograft acelluar dermis, amniotic membrane, Wharton's jelly, or any combination thereof; or
5. a micronized tissue graft comprising:
   a first membrane comprising modified amnion wherein the modified amnion comprises a first side which is an exposed basement membrane and a second side which is an exposed fibroblast layer, wherein the amnion is not decellularized; and
   one or more additional membranes sequentially layered such that the first additional membrane is layered adjacent to the exposed fibroblast layer,
   wherein the at least one or more additional membranes comprises amnion, chorion, allograft pericardium, allograft acelluar dermis, amniotic membrane, Wharton's jelly, or any combination thereof.

II. Applications of Tissue Grafts Composed Micronized Placental Tissue

The tissue grafts described herein have numerous medical applications. For example, tissue grafts that have at least one amnion layer can be used in numerous wound healing applications. Amnion contains growth factors such as EGF, bFGF, and PDGF that promotes wound healing and re-epithelialization. In one aspect, the application of the tissue grafts described herein where the epithelial layer of the skin is disrupted can be effective in delivering the growth factors directly to the injured site to promote healing. Amnion is a unique ECM due to the presence of collagen types IV, V and VII, which enables the amnion to bind water and swell.

Similarly, the intermediate tissue layer of the amniotic membrane is composed largely of glycoproteins and proteoglycans, which also enables the intermediate tissue layer to bind water. Thus, the tissue grafts when applied to the skin or wound help retain water in the skin, which facilitates wound healing. For example, cell migration within the wound healing cascade is facilitated in a hydrophilic environment. The intermediate layer is also composed of collagen types I, III, and IV. Type I collagen provides mechanical strength to skin by providing a major biomechanical scaffold for cell attachment and anchorage of macromolecules. Type III collagen provides elasticity. Hence, by adding the intermediate tissue layer tissue to the deep dermis it will not only increase the elasticity and scaffolding of the skin, it may make it feel softer. Another important component in the intermediate tissue layer that is beneficial to skin is proteoglycans. As discussed above, proteoglycans allow the intermediate tissue layer to bind water to such a large degree and swell considerably.

In other aspects, the grafts described herein can be used in orthopedic applications (i.e., sports medicine). Sports medicine includes the repair and reconstruction of various soft-tissue injuries in or around joints caused by traumas, or chronic conditions brought about by repeated motion, in active individuals and athletes. For example, sports medicine includes the treatment of a variety of different injuries associated with, but not limited to, shoulders, elbows, feet, ankles hand and wrists. In one aspect, the tissue grafts can be used to alleviate inflammation (e.g., tennis elbow, carpel tunnel, etc.). In other aspects, the tissue grafts can be applied to articular surfaces in order to provide medical benefits. For example, the tissue grafts can help reduce inflammation or swelling of an articular surface. In other aspects, the tissue grafts can help repair and/or regrow chondrocytes. In further aspects, the tissue grafts described herein can be used in other orthopedic applications such as aid in the repair of periostium; help repair ruptured/damaged bursa; help secure void filling material during bone repair; or in applications involving a subject's extremities (e.g., anti-adhesion barrier for small bone fixation, anti-adhesion barrier where metal plating or hardware is used, or help repair ruptured/damaged bursa).

In one aspect, the tissue grafts described herein are useful in enhancing or improving wound healing. The types of wounds that present themselves to physicians on a daily bases are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

The physician's goal when treating traumatic wounds is to heal the wound while allowing the patient to retain natural function in the area of the wound with minimal scaring and infection. If a wound becomes infected, it can lead to a loss of limb or life. For the most part, physicians heal these patients without incident. However, physicians dealing with chronic wounds are mainly concerned with closing the wound as quickly as possible to minimize the risk of an infection that could lead to loss of limb or life. Chronic wounds are wounds on patients that have comorbidities that complicate or delay the healing cascade. In one aspect, the tissue grafts described herein can function as a tissue regeneration template that delivers essential wound healing factors, extracellular matrix proteins and inflammatory mediators to help reduce inflammation, enhance healing, and reduces scar tissue formation. In this aspect, the micronized placental compositions described herein are used in treating wounds amenable to negative pressure technology, including burns and ulcers, such as chronic ulcers, diabetic ulcers, decubitus ulcers and the like.

In another aspect, the micronized placental tissue is used in conjunction with conventional treatments, including, but not limited to, negative pressure therapy, and may also be used in combination with matrices or scaffolds comprised of biocompatible materials, such as collagen, hyaluronic acid, gelatin or combinations thereof.

In another aspect, the tissue grafts described herein can be used to enhance wound healing and prevent scar formation as a result of a surgical incision. In one aspect, the tissue grafts can be applied to the open incision followed by suturing the incision. The tissue grafts are particularly useful where large incisions are produced by a surgical procedure. An example of such a procedure involves the treatment of spinal scoliosis, which requires a significant incision along the back of the subject. In one aspect, tissue grafts composed of an amnion/chorion laminate sandwich of micronized particles where the epithelium layer is intact are useful in the healing of surgical incisions with minimal scarring. With respect to wound healing and the prevention of scar formation, the tissue grafts described herein can be used in combination with other wound healing products.

In another aspect, the tissue grafts described herein are useful for addressing or alleviating complications to the spine and surrounding regions that occur after surgery. Acute and chronic spinal injuries and pain can be attributed to trauma and/or degenerative changes in the spinal column. For the degenerative patient, there is usually a progression of possible surgeries depending on the patient's symptoms and disease state. The first surgical option when conservative therapy has failed is a laminectomy or micro-discectomy. These minimally invasive procedures are intended to relieve the pain generator or stenosis of the spinal canal. If there is progression of the disease, then other surgeries may be necessary including, but not limited to, a spinal fusion. Spinal fusions may be achieved through several approaches: anterior (from the front through the abdomen), posterior (from the back), or lateral (through the side). Each approach has advantages and disadvantages. The goal is typically to remove the spinal disc, restore disc height and fuse the two spinal vertebrae together to limit motion and further degradation. There are also surgical options for the surgeon and patient to replace the spinal disc with an artificial disc. Spine trauma is typically treated by fusing the spine levels or if a vertebrae is crushed, the surgeon may choose to do a corpectomy and fusing across the levels that were affected.

In one aspect, the tissue grafts described herein are useful in preventing or reducing scar formation on the spine or near the spine and sealing dural tears. Scar formation at or near the spine after surgery can be very debilitating and possibly require subsequent operations to address the symptoms as discussed above. The term "anti-adhesion" is also used in the art to refer to the prevention of scar tissue at or near the spine. In other aspects, the tissue grafts described herein can be used as a protective barrier, where the composition protects the spinal dura from post-surgical trauma from the surrounding surgical site. For example, the composition can prevent damage to the spinal dura caused by sharp edges from newly cut bone such as vertebrae. In other aspects, the tissue grafts can be used for anterior lumbar interbody fusion, posterior lumbar interbody fusion trans-lumbar interbody fusion, anterior cervical discectomy and fusion, micro discectomy, spinal dura repair, and as a dura sealant to prevent CSF leakage.

Depending upon the surgical procedure, the tissue grafts can be applied directly to the spinal dura, the surrounding region of the spine to include nerve roots, or a combination thereof. Due to the unique structure of vertebrae, the tissue grafts can be placed and affixed at the appropriate position in the subject. The tissue grafts can also provide proximal and distal barrier coverage where the spinal lamina has been removed for exposure to the affected area.

The tissue grafts are useful in preventing or reducing scar formation that can result from a variety of surgical procedures associated with the spine. The tissue grafts can be used after any procedure in the neck, mid-back, or lower back. Depending upon the application, the epithelium of the amnion can be substantially removed. For example, in posterior procedures such as a laminectomy or discectomy, the epithelium layer of the amnion is substantially removed. Removal of the epithelial cell layer exposes the amnion's basement membrane layer, which increases cell signaling characteristics. This up regulation response enhances cellular migration and expression of anti-inflammatory proteins, which inhibits fibrosis. The spinal dura is typically left unprotected following posterior procedures.

In other aspects, the epithelial cell layer of the amnion is not removed. For example, in anterior procedures or modified anterior procedures such as Anterior Lumbar Interbody Fusion (ALIF) and Transforaminal Interbody Fusion (TLIF), the amnion epithelium layer is not removed and remains intact. In these aspects, the tissue grafts provide additional protection to the vertebral surgical site by maintaining separation from the peritoneum, larger vessels, and abdominal musculature. The tissue grafts serve as a reduced friction anatomical barrier against adhesions and scaring. For example, the tissue grafts can prevent scar tissue binding major blood vessels to the spine. This is a common problem with post-spinal surgery, which requires a second surgical procedure to address this.

In other aspects, the tissue grafts can be used to reduce inflammation related to gingivitis, periodontitis, mucositis, and peri-implantitis, treatment of periodontal intra-bony defects to regenerate new bone, periodontal ligament, and cementum, regenerate lost bone around dental implants, increase the amount of clinical attachment following osseous contouring, treatment of gingival recession, regeneration of interdental papilla, either through surgical reconstruction or by directly injecting the papilla to increase size and thickness, applied over the top of a barrier membrane or biocompatible mesh in alveolar vertical and horizontal bone augmentations, applied over the surgical site after primary closure to aid in healing, applied onto autograft, xenograft, alloplast, caderivic allograft or placental allograft soft tissue graft, either before, during, or after placement of the soft tissue graft in the treatment of gingival recession, increasing the amount of clinical attachment, gingival augmentations around teeth and dental implants, expanding the zone of keratinized tissue, thickening overlying gingival tissue in guided bone regeneration, mixed with a alloplast, xenograft, and or caderivic bone graft, either before, during, or after placement for use in the treatment of intrabony defects to regenerate new bone, periodontal ligament, and cementum, in guided bone regeneration regenerate lost bone around implants, site preservation, fenestration and dehiscence defects, primary and secondary alveolar ridge augmentations, sinus elevations, and gingival flap perforations. In applications involving dentin and pulpal tissue, reduce inflammation of pulpal tissue, treatment of endodontic lesions, pulpal regeneration, and injected into hollowed pulpal chamber prior to obturation in endodontic therapy. In applications involving oral mucosa tissue to reduce inflammation in oral lesions, the treatment of oral lesions, and applied onto autograft, xenograft, alloplast, caderivic allograft or placental allograft soft tissue graft either before, during, or after placement of the soft tissue graft to replace larger amounts of mucosal tissue lost through disease or traumatic injury.

In one aspect, the tissue grafts can be used to repair peripheral nerves. The tissue graft can be placed on a repaired nerve to prevent scar formation onto the healing nerve. The tissue grafts can also provide a protective enclosed environment for the repair to progress successfully. In other aspects, the tissue grafts can be manufactured into a nerve regeneration tube to guide nerve growth in a protective environment where the nerve ends cannot be re-approximated. Here, nerves can re-attach up to a certain distance if the ends are allowed to meet freely without other soft tissue interfering. In another aspect, the tissue grafts can be used to wrap nerve bundles after prostatectomy procedures. These nerves are responsible for erectile function and possible continence. The tissue grafts can be applied on the nerves to keep them from scarring and possibly damaging the nerves.

In another aspect, the tissue grafts can be used in obstetrics and gynecological (OB/GYN) surgical procedures involving the treatment of diseases that may be related to the fertility of the female, pain caused by the reproductive system or cancer in the reproductive system. These procedures include the removal of uterine fibroids (myomectomy), removal of ovarian cysts, tubal ligations, endometriosis treatments, removal of some cancerous or non-cancerous tumors, and vaginal slings. These procedures may be completed through a transvaginal, abdominal or laproscopical approach.

The tissue grafts can be used as a patch to reduce the amount of scar tissue in the reproductive system after a surgical procedure. Scar tissue is another form of fibrous tissue and may also contribute to fertility problems. The ability to minimize the amount of scaring on the ovaries, or within the fallopian tubes may help with post-operative fertility and even pain. In another aspect, the tissue grafts can be used to reline the uterine wall after severe endometriosis treatments and increase the patient's ability to conceive. In a further aspect, the tissue grafts can be used as an anti-adhesion barrier after removal of ovarian cyst or aid in the repair of vaginal wall erosion.

In other aspects, the tissue grafts can be used in cardiac applications. Angina is severe chest pain due to ischemia (a lack of blood, thus a lack of oxygen supply) of the heart muscle, generally due to obstruction or spasm of the coronary arteries (the heart's blood vessels). Coronary artery disease, the main cause of angina, is due to atherosclerosis of the cardiac arteries. Various open cardiac and vascular surgery procedures to remove atherosclerotic clots require the repair, reconstruction and closure of the vessel, and the support of a regenerative tissue patch to close and patch the surgical defect. Heart by-pass grafts and heart defect reconstruction (as part of an open-heart surgical procedure) also can benefit from a patch or graft to provide a buttress to soft-tissue weakness, tissue replacement if there is a lack of suitable tissue, and also the potential to reduce adhesions to the heart itself. The tissue grafts described herein can be used as a patch to support the repair of vascular and cardiac defects caused by operations and complications such as carotid artery repair, coronary artery bypass grafting, congenital heart disease, heart valve repair, and vascular repair (i.e. peripheral vessels).

The tissue grafts described herein can be used in general surgery procedures. For example, general surgical procedures include procedures related to the abdominal cavity. These include the intestines, stomach, colon, liver, gallbladder, appendix, bile ducts and thyroid glands. Procedures may include hernias, polypectomy, cancer removal, surgical treatment of Crohn's and ulcerative colitis. These procedures may be done open or laparoscopically. In other aspects, the tissue grafts can be used to facilitate closure of anastomosis, an anti-adhesion barrier for anastomosis, or an anti-adhesion barrier for hernia repair.

In other aspects, the tissue grafts can be used in ENT procedures. Tympanoplasty is performed for the reconstruction of the eardrum (tympanic membrane) and/or the small bones of the middle ear. There are several options for treating a perforated eardrum. If the perforation is from recent trauma, many ear, nose and throat specialists will elect to watch and see if it heals on its own. If this does not occur or frequent re-perforation occurs in the same area, surgery may be considered. Tympanoplasty can be performed through the ear canal or through an incision behind the ear. Here, the surgeon harvests a graft from the tissues under the skin around the ear and uses it to reconstruct the eardrum. The tissue grafts described herein can be used to prevent the additional trauma associated with harvesting the patients' own tissue and save time in surgery. In other aspects, the tissue grafts can be used as a wound covering after adenoidectomy, a wound cover after tonsillectomy, or facilitate repair of the Sniderian membrane.

In other aspects, the tissue grafts described herein can be used in plastic surgery procedures. Scar revision is surgery to improve or reduce the appearance of scars. It also restores function and corrects skin changes (disfigurement) caused by an injury, wound, or previous surgery. Scar tissue forms as skin heals after an injury or surgery. The amount of scarring may be determined by the wound size, depth, and location; the person's age; heredity; and skin characteristics including skin color (pigmentation). Surgery involves excision of the scar and careful closure of the defect. In one aspect, the tissue grafts described herein can be used as a patch to aid in the healing and prevention of scars; and keloid or cancer revision/removal where careful approximation of soft-tissue edges is not achievable and scar tissue can result. Additionally, the anti-inflammatory properties of the tissue grafts can enhance healing as well.

In other aspects, the tissue grafts can be used in ophthalmological applications (e.g., on-lay grafts ocular surface repair) or urological applications (e.g., facilitate closure of the vas deferens during vasectomy reversal or facilitate closure of the vas deferens resulting from trauma).

In one aspect, the tissue grafts can be used in cranial dura repair and replacement, in the elimination of a frenum pull, the regeneration of lost patella tissue, the repair of the Schneiderian membrane in the sinus cavity, soft tissue around dental implants, vestibuloplasty, and guided tissue regeneration.

In addition to the selection of the components used to make the tissue grafts, the size of the micronized particles present in the grafts can also vary depending upon their application. In certain aspects, micronized particles having a larger particle size can be used in several applications. For example, the micronized particles (e.g., micronized amnion/chorion tissue graft) having a particle size from 150 µm to 350 µm can be effective in wound healing where it is desirable to reduce or prevent scar formation and enhance soft tissue healing. In one aspect, the tissue grafts can be used to heal dermal wounds. The tissue grafts can be administered at any depth within the dermal tissue of a subject (e.g., sub-cutaneous, sub-dermal, etc.). In one aspect, the tissue grafts are useful in healing diabetic ulcers (e.g., foot ulcers). In other aspects, the dermal wounds can be tracking wounds (i.e., deep wounds that extend into the muscle tissue).

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Preparation of Micronized Placental Tissue

Amnion/chorion tissue grafts used here to produce the micronized particles were produced by the process described in U.S. 2008/0046095, which is incorporated by reference in its entirety. Tissue grafts (4 cm×3 cm) and two 9.5 mm steel grinding balls were placed in 50 mL vials and the vials subsequently sealed. The vials were placed in the Cryo-block, and the Cryo-block was placed in a Cryo-rack. The Cryo-rack was placed into a liquid nitrogen holding Dewar. Tissue samples were subjected to vapor phase cooling for no more than 30-60 minutes. The Cryo-rack was removed from the Dewar, and the Cryo-block was removed from the Cryo-rack. The Cryo-block was placed into the Grinder (SPEX Sample Prep GenoGrinder 2010) and set at 1,500 rpm for 20 minutes. After 20 minutes has elapsed, the tissue is inspected to ensure micronization. If necessary, the tissue can be placed back into the Dewar for an additional 30-60 minutes, and moved to the grinder for an additional 20 minutes to ensure sufficient micronization. Once the tissue is sufficiently micronized it is sorted using a series of American Standard ASTM sieves. The sieves were placed in the following order: 355 µm, 300 µm, 250 µm, 150 µm, and 125 µm. The micronized material was transferred from the 50 mL vials to the 355 µm sieve. Each sieve was agitated individually in order to thoroughly separate the micronized particles. Once the micronized particles have been effectively separated using the sieves, the micronized particles having particle sizes of 355 µm, 300 µm, 250 µm, 150 µm, and 125 µm were collected in separate vials.

Preparation of Tissue Grafts with Micronized Placental Tissue

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

A detailed description of suitable cross-linking agents and procedures is provided in U.S. Provisional Patent Application Ser. No. 61/683,697 filed Aug. 15, 2012 and entitled PLACENTAL TISSUE GRAFTS MODIFIED WITH A CROSS-LINKING AGENT AND METHODS OF MAKING AND USING THE SAME which application is incorporated herein by reference in its entirety.

A detailed description of reinforced placental tissue grafts is provided in U.S. Provisional Patent Application Ser. No. 61/683,699 filed Aug. 15, 2012 and entitled REINFORCED PLACENTAL TISSUE GRAFTS AND METHODS OF MAKING AND USING THE SAME which application is incorporated herein by reference in its entirety.

A detailed description of making and using micronized placental tissue and extracts thereof is provided in U.S. Provisional Patent Application Ser. No. 61/683,700 filed Aug. 15, 2012 and entitled MICRONIZED PLACENTAL TISSUE COMPOSITIONS AND METHODS OF MAKING AND USING THE SAME which application is incorporated herein by reference in its entirety.

What is claimed:

1. A dehydrated laminated tissue graft comprising two or more membrane layers wherein interposed between at least two of said membrane layers is a layer of micronized placental tissue particles, wherein:
    at least one of said membrane layers comprises an amnion membrane;
    wherein the other of said membrane layer(s) comprises at least one layer selected from the group consisting of an amnion membrane, a chorion membrane, an intermediate tissue layer, and a combination thereof;
    wherein the micronized placental tissue particles have a particle size less than 500 µm; and
    wherein at least one layer of amnion is not decellularized and comprises fibroblast cells and/or epithelial cells, or at least one layer of chorion is not decellularized.

2. The tissue graft of claim 1, wherein at least one of the membrane layers comprises an amnion membrane comprising a fibroblast layer.

3. The tissue graft of claim 1, wherein at least one of the membrane layers comprises an amnion membrane comprising an epithelial layer.

4. The tissue graft of claim 1, wherein at least one of the membrane layers comprises an amnion membrane substantially free of an epithelial layer.

5. The tissue graft of claim 1, wherein at least one of the membrane layers comprises an amnion membrane substantially free of a fibroblast layer.

6. The tissue graft of claim 1, wherein at least one of the membrane layers comprises an amnion membrane laminated with one or more additional membranes comprising amnion, chorion, or a combination thereof.

7. The tissue graft of claim 1, wherein at least one of the membrane layers comprises an amnion membrane laminated with two or more amnion membranes.

8. The tissue graft of claim 1, wherein at least one of the other said membrane layers comprises an amnion membrane.

9. The tissue graft of claim 1, wherein at least one of the other said membrane layers comprises a modified amnion membrane wherein the modified amnion membrane comprises a fibroblast layer.

10. The tissue graft of claim 1, wherein at least one of the other said membrane layers comprises a modified amnion membrane wherein the modified amnion membrane comprises a fibroblast layer and an epithelial layer.

11. The tissue graft of claim 1, wherein at least one of the other said membrane layers comprises an amnion membrane and an intermediate tissue layer.

12. The tissue graft of claim 1, wherein at least one of the other said membrane layers comprises a chorion membrane.

13. The tissue graft of claim 1, further comprising a second layer of micronized placental tissue.

14. The tissue graft of claim 1, wherein the micronized placental tissue is cross-linked.

15. The tissue graft of claim 1, wherein the micronized placental tissue further comprises a bioactive agent.

* * * * *